US005603325A

United States Patent [19]

Mazess et al.

[11] Patent Number: 5,603,325
[45] Date of Patent: Feb. 18, 1997

[54] ULTRASONIC DENSITOMETER WITH WIDTH COMPENSATION

[75] Inventors: Richard B. Mazess, Madison; Scott A. Wiener, Mount Horeb, both of Wis.

[73] Assignee: Lunar Corporation, Madison, Wis.

[21] Appl. No.: 466,495

[22] Filed: Jun. 6, 1995

Related U.S. Application Data

[63] Continuation-in-part of Ser. No. 397,027, Mar. 1, 1995, Pat. No. 5,483,965, which is a continuation of Ser. No. 72,799, Jun. 4, 1993, abandoned, which is a continuation-in-part of Ser. No. 895,494, Jun. 8, 1992, Pat. No. 5,343,863, which is a continuation-in-part of Ser. No. 772,982, Oct. 7, 1991, Pat. No. 5,119,820, which is a continuation of Ser. No. 343,170, Apr. 25, 1989, Pat. No. 5,054,490, which is a continuation-in-part of Ser. No. 193,295, May 11, 1988, Pat. No. 4,930,511.

[51] Int. Cl.$^6$ ..................................................... A61B 8/00
[52] U.S. Cl. .............................. 128/660.06; 128/661.03
[58] Field of Search ........................ 128/660.01, 660.06, 128/661.03; 73/597, 599

[56] References Cited

U.S. PATENT DOCUMENTS

| | | | |
|---|---|---|---|
| 2,439,130 | 8/1948 | Firestone | 128/661.03 |
| 3,345,863 | 10/1967 | Henry et al. | 128/661.03 |
| 3,477,422 | 11/1969 | Jurist, Jr. et al. | 128/661.03 |
| 3,587,561 | 6/1971 | Ziedonis | 128/661.03 |
| 3,648,685 | 3/1972 | Hepp et al. | 128/665 |
| 3,664,180 | 5/1972 | McDonald et al. | 73/598 |
| 3,713,329 | 1/1973 | Munger | 128/661.05 |
| 3,782,177 | 1/1974 | Hoop | 73/643 |
| 3,847,141 | 11/1974 | Hoop | 128/660.01 |
| 4,048,986 | 9/1977 | Ott | 128/653.1 |
| 4,056,970 | 11/1977 | Sellish | 73/629 |
| 4,105,018 | 8/1978 | Greenleaf et al. | 73/597 |
| 4,138,999 | 2/1979 | Eckhart et al. | 128/661.03 |
| 4,217,912 | 8/1980 | Hubmann et al. | 128/774 |
| 4,233,845 | 11/1980 | Pratt, Jr. | 73/865.4 |
| 4,235,243 | 11/1980 | Saha | 128/740 |
| 4,250,895 | 2/1981 | Lees | 128/776 |
| 4,316,183 | 2/1982 | Palmer et al. | 340/621 |
| 4,361,154 | 11/1982 | Pratt, Jr. | 128/660.01 |
| 4,421,119 | 12/1983 | Pratt, Jr. | 128/660.01 |
| 4,476,873 | 10/1984 | Sorenson et al. | 128/661.01 |
| 4,522,068 | 6/1985 | Smith | 73/32 A |
| 4,530,360 | 7/1985 | Duarte | 607/51 |

(List continued on next page.)

FOREIGN PATENT DOCUMENTS

| | | | |
|---|---|---|---|
| 2318420 | 7/1975 | France . | |
| 219853 | 3/1959 | U.S.S.R. . | |
| 123748 | 9/1968 | U.S.S.R. . | |
| WO80/02796 | 6/1980 | WIPO . | |
| 8002796 | 12/1980 | WIPO | 128/661.03 |

OTHER PUBLICATIONS

C. M. Langton, S. B. Palmer, and R. W. Porter, "The Measurement of Broadband Ultrasonic Attenuation in Cancellous Bone", *Eng. Med.*, vol. 13, pp. 89–91 1984.

S. Lees, "Sonic Properties of Mineralized Tissue", *Tissue Characterization with Ultrasound*, CRC Publication 2, pp. 207–226 (1986).

J. D. Craven, M. A. Constantini, M. A. Greenfield, and R. Stern, "Measurement of the Velocity of Ultrasound in Human Cortical Bone and Its Potential Clinical Importance", *Investigative Radiology*, vol. 8, pp. 72–77 (1973).

(List continued on next page.)

*Primary Examiner*—Francis Jaworski
*Attorney, Agent, or Firm*—Quarles & Brady

[57] ABSTRACT

An ultrasound densitometer is disclosed in which ultrasonic transducers are located spaced apart in a water bath into which the heel of a person may be inserted. Attenuation and time of flight of an ultrasonic pulse are determined and combined to reduce the effect of heel width on the measurement without physically measuring the heel width. Bladders with selected coupling gels may be used to adjust the region at which the heel width effects are most reduced. A C-brace used to hold the transducers independent of the water bath permits their removal for servicing without upsetting their alignment and separation when reinstalled.

14 Claims, 10 Drawing Sheets

U.S. PATENT DOCUMENTS

| | | | |
|---|---|---|---|
| 4,597,292 | 7/1986 | Fujuii et al. | 73/599 |
| 4,669,482 | 6/1987 | Ophir | 128/661.03 |
| 4,774,959 | 10/1988 | Palmer | 128/660.06 |
| 4,913,157 | 4/1990 | Pratt et al. | 128/661 |
| 4,930,511 | 6/1990 | Rossman et al. | 128/661.03 |
| 5,014,970 | 5/1991 | Osipov | 5/652 |
| 5,119,820 | 6/1992 | Rossman et al. | 128/661.03 |
| 5,218,963 | 6/1993 | Mazess | 128/661.03 |
| 5,259,384 | 11/1993 | Kaufman et al. | 128/660.06 |
| 5,335,661 | 8/1994 | Koblanski | 128/661.03 |
| 5,348,009 | 9/1994 | Ohtomo et al. | 128/661.03 X |
| 5,349,959 | 9/1994 | Wiener et al. | 128/661.03 |
| 5,452,722 | 9/1995 | Langton | 128/661.03 X |

OTHER PUBLICATIONS

C. Rich, E. Klink, R. Smith, B. Graham, and P. Ivanovich, "Sonic Measurement of Bone Mass", *Progress in development of Methods in Bone Densitometry*, pp. 137–146, (NASA 1966).

M. Greenspan and C. E. Tschiegg, "Sing–Around Ultrasonic Velocimeter for Liquids", *The Review of Scientific Instruments*, vol. 28, No. 11, pp. 897–901 (1957).

W. Abendschein and G. W. Hyatt, "Ultrasonics and Selected Physical Properties of Bone", *Clinical Orthopedics and Related Research*, No. 69, pp. 294–301 (1970).

M. Gerlanc, D. Haddad, G. Hyatte, J. Langloh, and P. St. Hilaire, "Ultrasonic Study of Normal and Fractured Bone", *Clinical Orthopedics and Related Research* pp. 175–180, (1975).

B. Martin and R. R. Haynes, "The Relationship Between the Speed of Sound and Stiffess of Bone", *Biomechanics Laboratories*, West Virginia University (1970).

J. M. Hoop and W. N. Clotfleter, "Ultrasonic Bone Density Measurements", Marshall Space Flight Center, The Fall Conference of the American Society for Nondestructive Testing (1970).

K. H. Okumura, "Preventive Diagnosis of Breakdown", Massachusetts Institute of Technology (1978).

W. N. McDicken, The Physics of Ultrasound in Diagnostic Ultrasonics, pp. 35–61 (1976).

Lees, S. and C. Davidson, "The Role of Collagen in the Elastic Processing of Calcified Tissues", *C. Journal of Biomechanics*, vol. 10, No. 7 (1977), pp. 473–486.

Van Venrooij, G. "Measurement of Ultrasound Velocity in Human Tissue", *Ultrasonics*, Oct. (1971), pp. 240–242.

Lang, S. "Ultrasonic Method for Measuring Elastic Coefficients of Bone and Results on Fresh and Dried Bovine Bones", *IEEE Transactions on Bio–Medical and Engineering*, vol. BME–17, No. 2 (Apr. 1970), pp. 101–105.

Martin B. and R. Haynes, "The Investigation of Bone's Substructure Using Meganertz Sound and a Porous Model", *ASME Publication* (Dec. 3, 1970).

Brown, S. A. and M. B. Mayor, "Ultrasonic Prediction of Delayed or Nonunion of Fractures", *Proceedings of the Fifth New England Bioengineering Conference* (Apr. 15, 1977), pp. 229–233.

Brown, S. A. and M. B. Mayor, "UltrasonicAssessment of Early Callus Formation, Biomedical Engineering", vol. 11, No. 4 (Apr. 1976), pp. 124–128.

Yamada, H., "Strength of Biological Materials", pp. 53–57 (1970).

Wells, P. N. T., "Physical Principles of Ultrasonic Diagnosis", *Academic Press*, London (1969), pp. 1–27.

Mather, B. S., "Comparison of Two Formulae in Vivo Prediction of Strength of the Femur", *Aerospace Medicine*, vol. 38, No. 12 (Dec. 1967), pp. 1270–1272.

Rossman, P. J. "Measurements of Ultrasonic Velocity and Attenuation in the human os calcis and their relationship photon absorptiometry bone mineral measurements." Master's Thesis, University of Wisconsin–Madison, 1987.

C. M. Langton, et al., "A Contact Method for the Assessment of Ultrasonic Velocity and Broadband Attenuation in Cortical and Cancellous Bone", Clin. Phys. Physiol. Meas., 1990, vol. 11, No. 3, 243–249. Printed in the UK.

J. Lawrence Katz, et al., "The Structure and Anisotropic Mechanical Properties of Bone", IEEE Transactions on Biomedical Engineering BME–31 (1984) Dec., No. 12, New York, USA.

Robert E. Holm, et al., Use Discrete Fourier Transforms to Simplify Signal Processing, EDN Apr. 28, 1983.

V. Poll, et al., Broadband Ultrasonic Attenuation in the *os calcis* and Single Photon Absorptiometry in the Distal Forearm: a Comparative Study, Clin. Phys. Physiol. Meas. 1986, vol. 7, No. 4, 375–379, Printed in Great Britain.

Shukla, Shailendra S., et al., A Study of the Homogeneity of the Trabecular Bone Mineral Density, Med. Phys. 14(4) Jul./Aug. 1987.

Anast, George T., et al., Ultrasonic Technique for the Evaluation of Bone Fractures, Biol., Eng. Soc. vol. 11, No. 4 Apr. 1976.

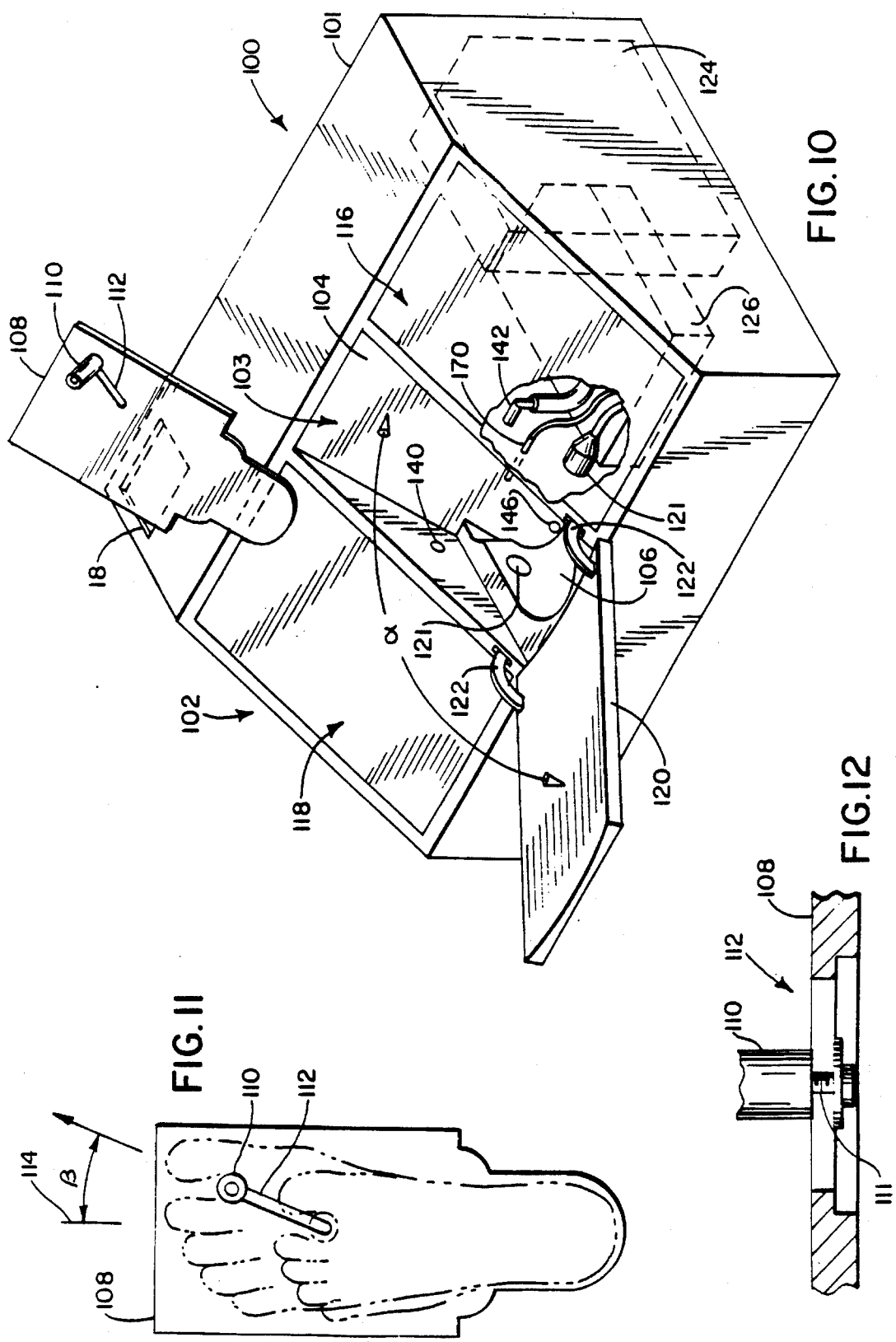

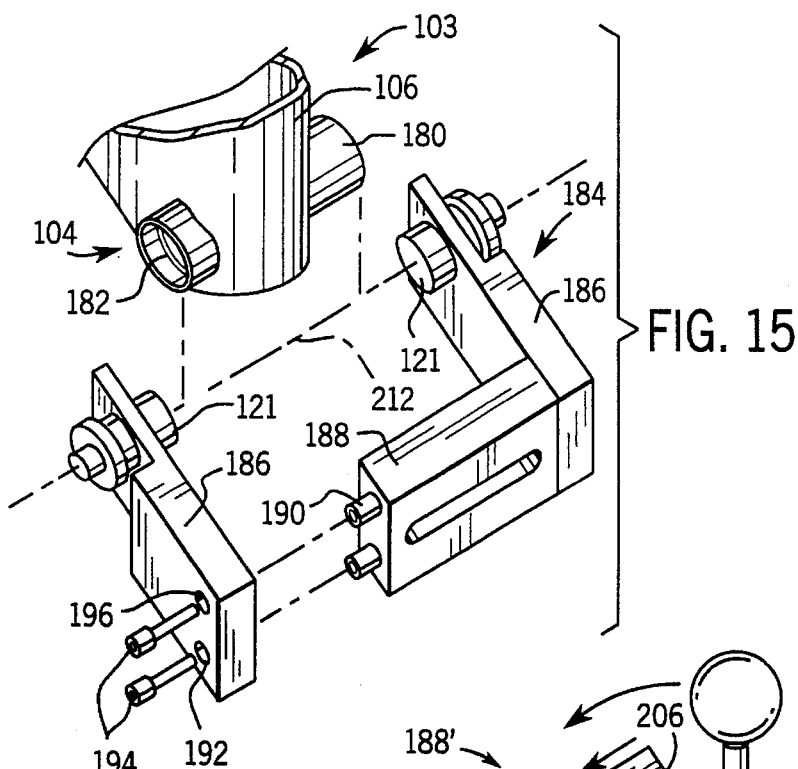
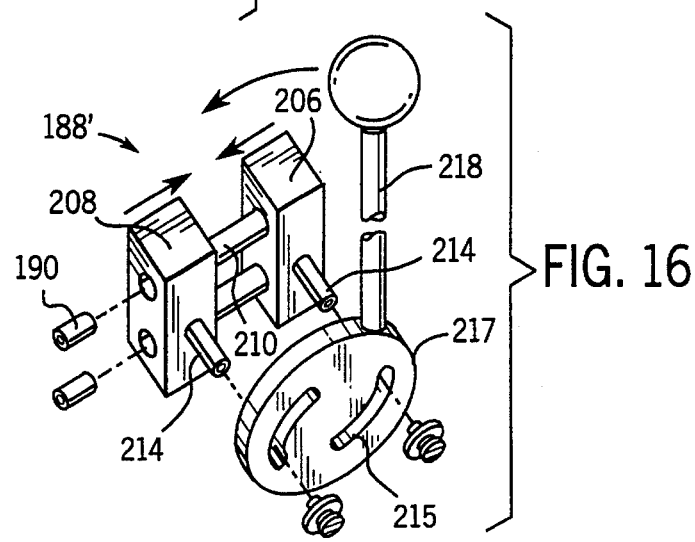
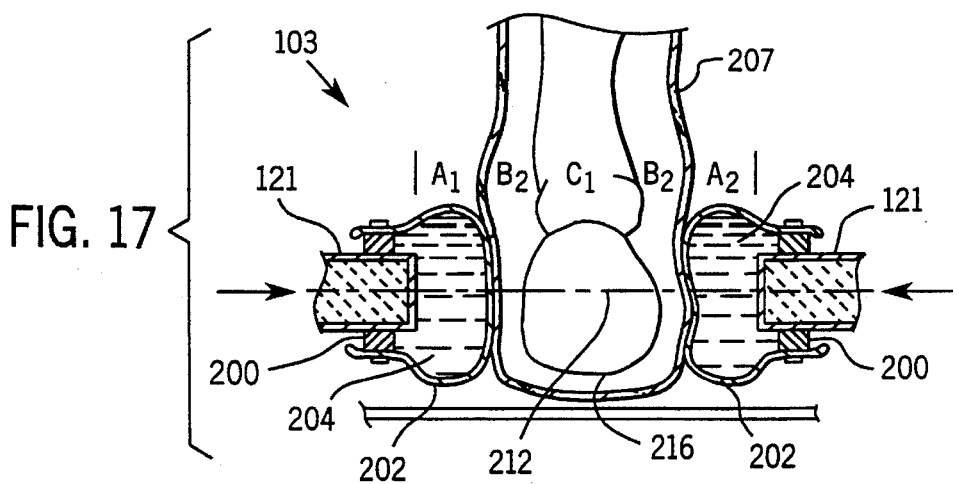
FIG. 15
FIG. 16
FIG. 17

ULTRASONIC DENSITOMETER WITH WIDTH COMPENSATION

CROSS-REFERENCE TO RELATED APPLICATION

The application is a continuation in part of U.S. patent application Ser. No. 08/397,027 filed Mar. 1, 1995 now issued as U.S. Pat. No. 5,483,965 which is a continuation of patent application Ser. No. 08/072,799 filed Jun. 4, 1993, abandoned, which is a continuation in part of U.S. patent application Ser. No. 07/895,494 filed Jun. 8, 1992, now U.S. Pat. No. 5,343,863, which is a continuation in part of U.S. patent application Ser. No. 07/772,982 filed Oct. 7, 1991, now U.S. Pat. No. 5,119,820, which is a continuation of U.S. patent application Ser. No. 07/343,170 filed Apr. 25, 1989, now U.S. Pat. No. 5,054,490, which is a continuation in part of patent application Ser. No. 07/193,295 filed May 11, 1988, now U.S. Pat. No. 4,930,511.

BACKGROUND OF THE INVENTION

1. Field of the Invention

The present invention relates to devices which are used for measuring the density of members, such as bones, and more particularly to devices which utilize ultrasonic acoustic signals to measure the physical properties and integrity of the members.

2. Description of the Prior Art

Various devices presently exist which may be used to measure the physical properties and integrity of a member such as a bone. Non-invasive density measuring devices can be used to determine cumulative internal damage caused by micro-crushing and micro-fracturing occurring in the bones of humans or animals such as race horses. Additionally, osteoporosis, or loss of bone mineralization, detection in humans and its cure or prevention are increasingly becoming areas of intense medical and biological interest. As the average age of the human population increases, a greater number of patients are developing complications due to rapid trabecular bone loss.

U.S. Pat. No. 3,847,141 to Hoop discloses a device for measuring the density of a bone structure, such as a finger bone or heel bone, to monitor the calcium content thereof. The device includes a pair of opposed spaced ultrasonic transducers which are held within a clamping device clamped on the bone being analyzed. A pulse generator is coupled to one of the transducers to generate an ultrasonic sound wave which is directed through the bone to the other transducer. An electric circuit couples the signals from the receive transducer back to the pulse generator for retriggering the pulse generator in response to those signals. The pulses therefore are produced at a frequency proportional to the transit time that the ultrasonic wave takes to travel through the bone structure, which is directly proportional to the speed of sound through the bone. The speed of sound through a bone has been found to be proportional to the density of the bone. Thus the frequency at which the pulse generator is retriggered is proportional to the density of the bone.

Another device and method for establishing in vivo the strength of a bone is disclosed in U.S. Pat. Nos. 4,361,154 and 4,421,119 to Pratt, Jr. The device includes a launching transducer and a receiving transducer which are connected by a graduated vernier and which determine the speed of sound through the bone to determine its strength. The vernier is used to measure the total transit distance between the surfaces of the two transducers.

Lees (Lees, S. (1986) Sonic Properties of Mineralized Tissue, *Tissue Characterization With Ultrasound*, CRC publication 2, pp. 207–226) discusses various studies involving attenuation and speed of sound measurements in both cortical and spongy (cancellous or trabecular) bone. The results of these studies reveal a linear relationship between the wet sonic velocity and wet cortical density, and between the dry sonic velocity and the dry cortical density. The transit times of an acoustic signal through a bone member therefore are proportional to the bone density. Langton, et al. (Langton, C. M., Palmer, S. D., and Porter, S. W., (1984). The Measurement of Broad Band Ultrasonic Attenuation in Cancellous Bone, *Eng. Med.*, 13, 89–91) published the results of a study of ultrasonic attenuation versus frequency in the os calcis (heel bone) that utilized through transmission techniques. These authors suggested that attenuation differences observed in different subjects were due to changes in the mineral content of the os calcis. They also suggested that low frequency ultrasonic attenuation may be a parameter useful in the diagnosis of osteoporosis or as a predictor of possible fracture risk.

SUMMARY OF THE INVENTION

The velocity of sound through bone in vivo can be determined by first timing the propagation of the sound through the bone and second accurately measuring the width of the bone through which the sound propagated. Normally, propagation time can be accurately measured but the measurement of width of the bone is far more difficult. This is because the bone is surrounded by soft tissue and because its shape is irregular.

The present inventors believe that errors in the measurement of width of the bone significantly limit the precision of ultrasonic bone densitometry. Accordingly, the present invention, which times the propagation of ultrasonic sound through a human heel, foregoes measurement of the width of the heel and instead assumes a standard heel width. It is believed that this assumption introduces less error than that which would be introduced by an attempt to accurately measure the irregular and inaccessible heel bone.

Further, the present invention further recognizes that the time of flight of sound through the bone and the attenuation of sound through the bone can be represented as independent functions of both bone quality and bone width.

As such, a proper combination of these functions should provide a measure of bone quality independent of bone width—just as two independent equations of two variables may be solved for one variable alone.

In this regard, the present invention evaluates bone quality of a patient in vivo by positioning the patient's heel along a path of predetermined length greater than the width of the heel. A measure of transit time of an ultrasonic pulse for the predetermined path length is then made through both a standard coupling medium (bridging the gap between the transducers and the heel) and the heel, the coupling medium conducting sound at a predetermined first sound speed. A measure of attenuation of the ultrasonic pulse through the same path is also made, the coupling medium attenuating sound at a predetermined first attenuation rate.

The functional relationship between the measure of attenuation and bone quality and heel width, for the predetermined length and the coupling medium, and the functional relationship between the measure of transit time and bone quality and bone heel are then evaluated for the predetermined length and the coupling medium, to identify a single pair of common bone quality and heel width values related to both of the measures of attenuation and transit time. This common bone quality value is substantially independent of the width of the heel.

It is therefore one object of the invention to provide a measurement of bone quality that is largely independent of the width of the bone being measured and which eliminates the need to make variable and often inaccurate bone width determinations.

The functional dependence between ultrasonic propagation time and bone width is largely determined by the selection of the coupling material used to provide a path between ultrasound transducers and the tissue of the heel. For example, if the speed of sound in the coupling material is greater than that in the bone, then a wider heel, displacing more coupling material, will cause an apparent decrease in the velocity of the sound (1/propagation time) along the path. Similarly, increases in the width of the heel can increase the attenuation of the sound. Selection of the proper coupling medium, which provides the heel width dependency of these measures, can improve the measurement of bone quality by permitting control of the relative contribution of the attenuation measurement and the time of flight measurement used to deduce bone quality. Importantly, in the cases where the time of flight or attenuation through the bone matches the sound speed or attenuation through the coupling medium, cancellation of heel width cannot be done. Proper selection of the coupling medium can move these points of non-cancellation away from the range of critical measurement values.

To facilitate a flexible choice of the coupling medium, bladders may surround the ultrasonic transducers and bridge the gap between the transducers and the heel. Specifically, the bone densitometer employs a first and second ultrasonic transducer having opposed faces and positionable at a predetermined fixed separation greater than a typical human heel. First and second flexible bladders are attached to the first and second ultrasonic transducers to contain about the opposed faces a coupling material having a sound speed greater than that of bone of a reference quality. Pulse launching and receiving circuitry launches an ultrasonic pulse between the first and second ultrasonic transducers through the first and second bladders and through a width of the heel and receives the same to produce a measure of transit time and of attenuation of the ultrasonic pulse. Finally, a weighting circuit weights the transit time relative to the attenuation to provide a measure of bone quality having reduced sensitivity to a width of the heel. The bladders may be filled with a material having an arbitrary predetermined acoustic property to provide the desired cancellation of width effects in the desired range.

Thus, it is another object of the invention to provide a densitometer that optimizes the previously described heel width cancellation technique.

In another aspect of the invention an independent C-clamp structure is used to hold the ultrasonic transducers in opposition with fixed separation and orientation as required by the above techniques. The C-clamp has a separable joint to permit matched transducer pairs to be removed and replaced.

Specifically, the ultrasonic densitometer may include a water basin sized to receive the heel of a patient, the basin having opposed first and second openings along an axis intersecting the patient's heel when the patient's heel is in place within the basin. First and second ultrasonic transducer are slidably received in the first and second opening, respectively. A C-brace, removable from the water basin, has a first and second arm attached to the first and second transducer. The C-brace also has a separable joint so that the first and second arm may be moved apart for insertion of the first and second transducers into the first and second openings. The separable joint further has alignment surfaces causing the first and second ultrasonic transducer to be returned to a predetermined alignment and separation when the alignment surfaces abut.

It is thus another object of the invention to provide a highly accurate alignment of the ultrasonic transducers necessary for the above described width compensation technique that still permits removal and repair of the transducers.

Other objects, features and advantages of the invention will be apparent from the following detailed description taken in conjunction with the accompanying drawings wherein a preferred embodiment of the invention has been selected for exemplification.

BRIEF DESCRIPTION OF THE DRAWINGS

FIG. 10 is a perspective view of an alternative embodiment of the present invention showing a basin for receiving a patient's foot and having integral opposed ultrasonic transducers;

FIG. 11 is a plan view of a foot plate and toe peg used with the embodiment of FIG. 10;

FIG. 12 is a cross-sectional detail of the foot plate of FIG. 11 showing the method of attaching the sliding toe peg of the foot plate;

FIG. 15 is an exploded view of the underside of the foot basin of FIG. 10 showing a C-clamp for holding the opposed ultrasonic transducers in precise alignment and separation;

FIG. 16 is a perspective detailed view of the shank of the C-clamp of FIG. 15 showing a lever for moving the separation of the transducers between an open and precisely separated closed position;

FIG. 17 is a cross-section of a human heel and ultrasonic transducers of the basin of FIG. 10 showing flexible liquid filled bladders surrounding the transducers and providing a coupling path between the transducers and the heel;

DESCRIPTION OF THE PREFERRED EMBODIMENT

Caliper Embodiment

Figure 1:
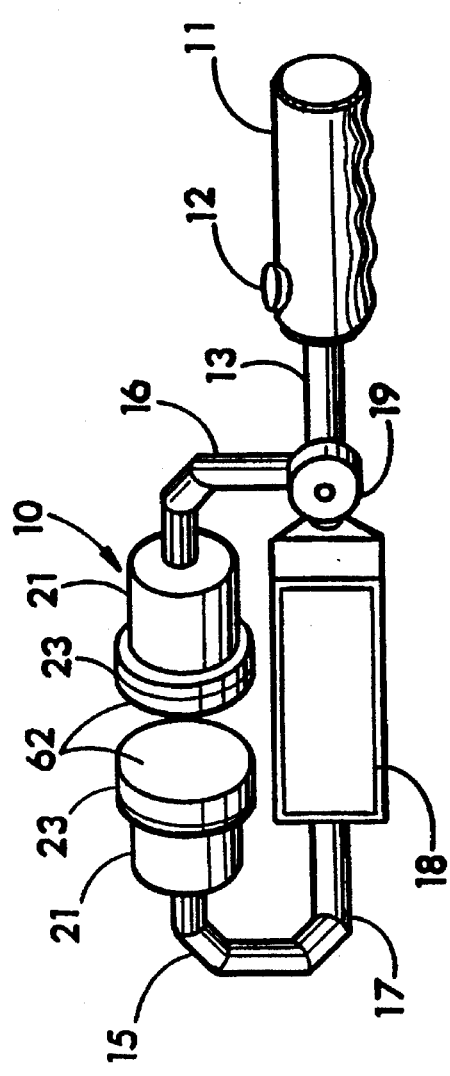
FIG. 1 is a perspective view of the ultrasound densitometer device constructed in accordance with the present invention.

Referring more particularly to the drawings, wherein like numbers refer to like parts, FIG. 1 shows a portable ultrasound densitometer 10 for measuring the physical properties and integrity of a member, such as a bone, in vivo. The densitometer 10 as shown in FIG. 1 includes a handle 11 with actuator button 12. Extending linearly from the handle 11 is a connection rod 13. The densitometer 10 also includes a fixed arm 15 and an adjustable arm 16. The fixed arm 15 preferably is formed continuously with the connection rod 13, and therefore is connected to an end 17 of the connection rod 13. The adjustable arm 16 is slidably mounted on the connection rod 13 between the handle 11 and a digital display 18 mounted on the rod 13. The knob 19 may be turned so as to be locked or unlocked to allow the adjustable arm 16 to be slid along the connection rod 13 so that the distance between the arms 15 and 16 may be adjusted.

Figure 3:
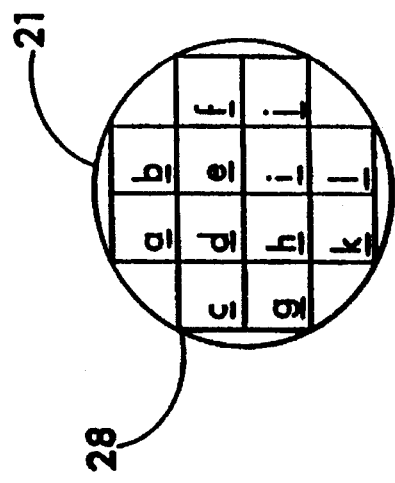
FIG. 3 is a front view of a transducer face from which acoustic signals are transmitted or by which acoustic signals are received, the face of the other transducer being the mirror image thereof.
Figure 2:
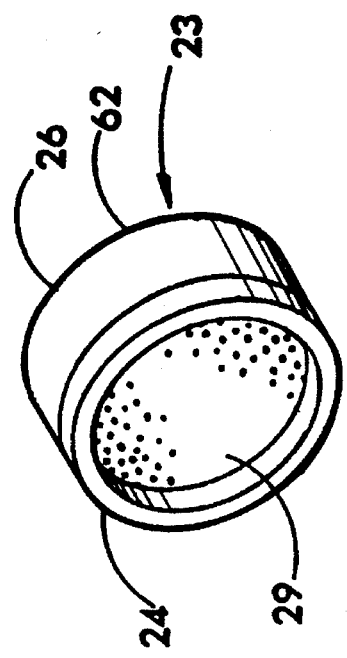
FIG. 2 is a perspective view of an acoustic coupler, two of which are shown in FIG. 1.

Connected at the end of the fixed arm 15 is a first (left) transducer 21 and at the end of the adjustable arm 16 is a second (right) transducer 21. As shown in FIGS. 1 and 2, each of the transducers 21 has mounted on it a respective compliant acoustic coupler 23 to acoustically couple the transducer to the object being tested. The acoustic coupler 23 includes a plastic ring 24 and attached pad 26 formed of urethane or other compliant material. FIG. 3 shows a face 28 of the first (left) transducer 21 which is normally hidden behind the compliant pad 26 of the acoustic coupler 23. The transducer face 28 normally abuts against the inner surface 29 of the pad 26 shown in FIG. 2. The transducer face 28 shown in FIG. 3 includes an array of twelve transducer elements labeled a–l. The second (right) transducer 21 includes a face 28 which is the mirror image of that shown in FIG. 3.

Figure 4:
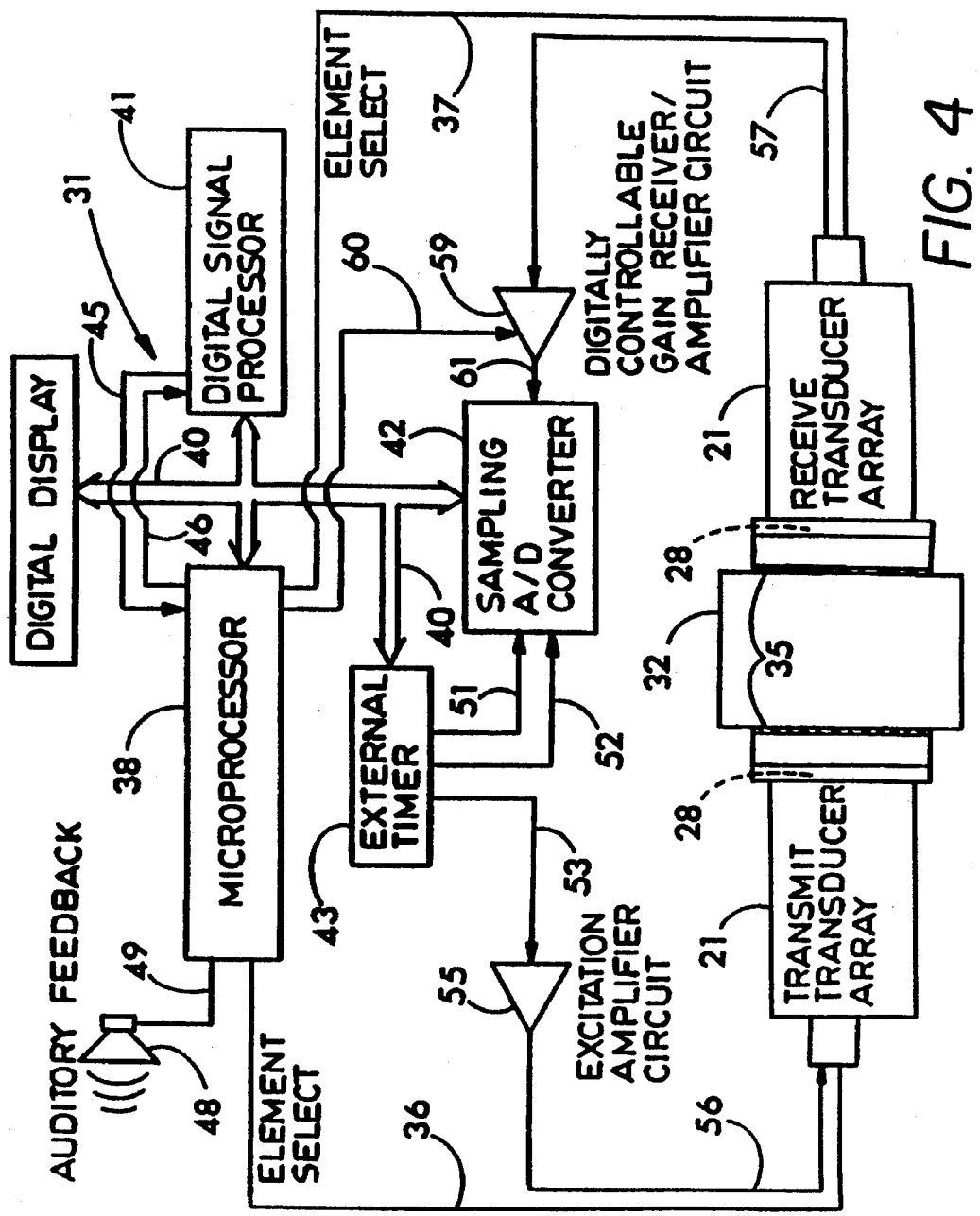
FIG. 4 is a schematic block diagram view of the circuitry of the ultrasound densitometer device constructed in accordance with the present invention.

FIG. 4 generally shows in schematic fashion the electronic circuitry 31 of the densitometer 10, which is physically contained in the housing of the digital display 18. An object 32 is placed between the two transducers 21 so that acoustic signals may be transmitted through the object. This object 32 represents a member, such as a bone, or some material with known acoustic properties such as distilled water or a neoprene reference block. As shown in the embodiment illustrated in FIG. 4, the leftmost transducer 21 is a transmit transducer and the rightmost transducer 21 a receive transducer. In fact though, either or both of the transducers 21 may be a transmit and/or receive transducer.

The transmit and receive transducers 21 of the circuit of FIG. 4 are connected by element select signals 36 and 37 to a microprocessor 38. The microprocessor 38 is programmed to determine which one of the respective pairs of transducer elements a through l are to be transmitting and receiving at any one time. This selection is accomplished by the element select signal lines 36 and 37, which may be either multiple signal lines or a serial data line to transmit the needed selection data to the transducers 21. The microprocessor 38 is also connected by a data and address bus 40 to the digital display 18, a digital signal processor 41, a sampling analog to digital converter 42, and a set of external timers 43. The microprocessor 38 has "on board" electrically programmable non-volatile random access memory (NVRAM) and, perhaps as well, conventional RAM memory, and controls the operations of the densitometer 10. The digital signal processor 41 has "on board" read-only memory (ROM) and performs many of the mathematical functions carried out by the densitometer 10 under the control of the microprocessor 38. The digital signal processor 41 specifically includes the capability to perform discrete Fourier transforms, as is commercially available in integrated circuit form presently, so as to be able to convert received waveform signals from the time domain to the frequency domain. The microprocessor 38 and digital signal processor 41 are interconnected also by the control signals 45 and 46 so that the microprocessor 38 can maintain control over the operations of the digital signal processor 41 and receive status information back. Together, the microprocessor 38 and the digital signal processor 41 control the electrical circuit 31 so that the densitometer 10 can carry out its operations, which will be discussed below. An auditory feedback mechanism 48, such as an audio speaker, can be connected to the microprocessor 38 through an output signal 49.

The external timer 43 provides a series of clock signals 51 and 52 to the A/D converter 42 to provide time information to the A/D converter 42 so that it will sample at timed intervals electrical signals which it receives ultimately from the transmit transducer, in accordance with the program in the microprocessor 38 and the digital signal processor 41. The external timer 43 also creates a clock signal 53 connected to an excitation amplifier 55 with digitally controllable gain. Timed pulses are generated by the timer 43 and sent through the signal line 53 to the amplifier 55 to be amplified and directed to the transmit transducer 21 through the signal line 56. The transmit transducer 21 converts the amplified pulse into an acoustic signal which is transmitted through the object or material 32 to be received by the receive transducer 21 which converts the acoustic signal back to an electrical signal. The electrical signal is directed through output signal 57 to a receiver amplifier 59 which amplifies the electrical signal.

The excitation amplifier circuit 55 is preferably a digitally controllable circuit designed to create a pulsed output. The amplification of the pulse can be digitally controlled in steps from one to ninety-nine. In this way, the pulse can be repetitively increased in amplitude under digital control until a received pulse of appropriate amplitude is received at the receiver/amplifier circuit 59, where the gain is also digitally adjustable.

Connected to the receiver amplifier circuit 59 and integral therewith is a digitally controllable automatic gain control circuit which optimizes the sensitivity of the receive transducer 21 and the amplifier circuit 59 to received acoustic signals. The microprocessor 38 is connected to the amplifier circuit and automatic gain control 59 through signal line 60 to regulate the amplification of the amplifier circuit and gain control 59. The amplified electric signals are directed through lead 61 to the A/D converter 42 which samples those signals at timed intervals. The A/D converter 42 therefore in effect samples the received acoustic signals. As a series of substantially identical acoustic signals are received by the receive transducer 21, the A/D converter 42 progressively samples an incremental portion of each successive signal waveform. The microprocessor 38 is programmed so that those portions are combined to form a digital composite waveform which is nearly identical to a single waveform. This digitized waveform may be displayed on the digital display 18, or processed for numerical analysis by the digital signal processor 41.

The densitometer constructed in accordance with FIGS. 1–4 can be operated in one or more of several distinct methods to measure the physical properties of the member, such as integrity or density. The different methods, as described in further detail below, depend both on the software programming and the operation of the microprocessor 34 as well as the instructions given to the clinician as to how to use the densitometer. The different methods of use may all be programmed into a single unit, in which case a user-selectable switch may be provided to select the mode of operation, or a given densitometer could be constructed to be dedicated to a single mode of use. In any event, for the method of use of the densitometer to measure the physical properties of a member to be fully understood, it is first necessary to understand the internal operation of the densitometer itself.

In any of its methods of use, the densitometer is intended to be placed at some point in the process on the member whose properties are being measured. This is done by placing the transducers 21 on the opposite sides of the member. To accomplish this, the knob 19 is loosened to allow the adjustable arm 16 to be moved so that the transducers 21 can be placed on opposite sides of the member, such as the heel of a human patient. The outside surfaces of the pads 26 can be placed against the heel of the subject with an ultrasound gel 35 or other coupling material placed between the pads 26 and subject 32 to allow for improved transmission of the acoustic signals between the member 32 and transducers 21. Once the transducers 21 are properly placed on the member, the knob 19 may be tightened to hold the adjustable arm 16 in place, with the transducers 21 in spaced relation to each other with the member 32 therebetween. The actuator button 12 may then be pressed so that acoustic signals will be transmitted through the member 32 to be received by the receive transducer 21. The electronic circuit of FIG. 4 receives the electrical signals from the receive transducer 21, and samples and processes these signals to obtain information on the physical properties and integrity of the member 32 in vivo. The microprocessor 38 is programmed to indicate on the digital display 18 when this information gathering process is complete. Alternatively, the information may be displayed on the digital display 18 when the information gathering process is completed. For example, the transit time of the acoustic signals through the member 32 could simply be displayed on the digital display 18.

Figure 5:
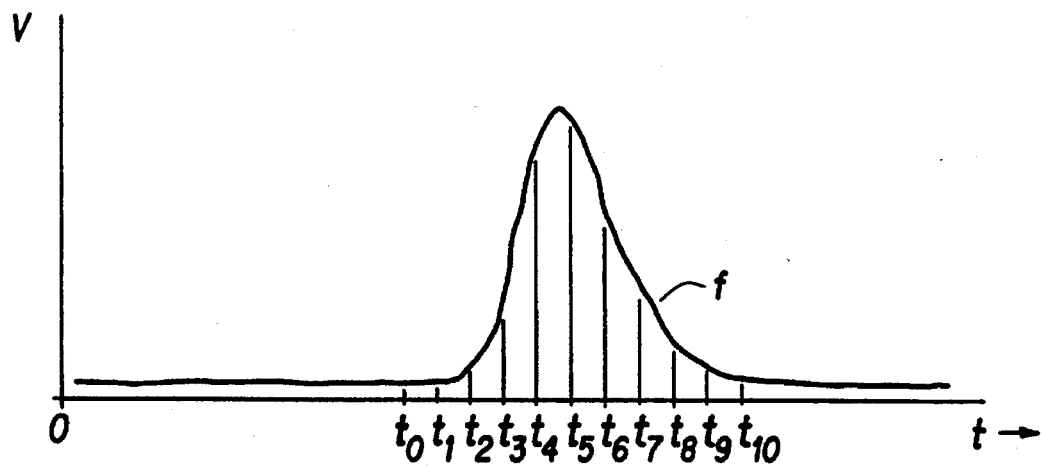
FIG. 5 illustrates the method of sampling a received waveform used by the circuit of FIG. 4.

Considering in detail the operation of the circuitry of FIG. 4, the general concept is that the circuitry is designed to create an ultrasonic pulse which travels from transmit transducer 21 through the subject 32 and is then received by the receive transducer 21. The circuitry is designed to both determine the transit time of the pulse through the member 32, to ascertain the attenuation of the pulse through the member 32, and to be able to reconstruct a digital representation of the waveform of the pulse after it has passed through the member 32, so that it may be analyzed to determine the attenuation at selected frequencies. To accomplish all of these objectives, the circuitry of FIG. 4 operates under the control of the microprocessor 38. The microprocessor 38 selectively selects, through the element select signal lines 36, a corresponding pair or a group of the elements a through l on the face of each of the transducers 21. The corresponding elements on each transducer are selected simultaneously while the remaining elements on the face of each transducer are inactive. With a given element, say for example element a selected, the microprocessor then causes the external timer 43 to emit a pulse on signal line 53 to the excitation amplifier circuit 55. The output of the excitation amplifier 55 travels along signal line 56 to element a of the transmit transducer 21, which thereupon emits the ultrasonic pulse. The corresponding element a on the receive transducer 21 receives the pulse and presents its output on the signal line 57 to the amplifier circuit 59. What is desired as an output of the A/D converter 42 is a digital representation of the analog waveform which is the output of the single transducer element which has been selected. Unfortunately, "real time" sampling A/D converters which can operate rapidly enough to sample a waveform at ultrasonic frequencies are relatively expensive. Therefore it is preferred that the A/D converter 42 be an "equivalent time" sampling A/D converter. By "equivalent time" sampling, it is meant that the A/D converter 42 samples the output of the transducer during a narrow time period after any given ultrasonic pulse. The general concept is illustrated in FIG. 5. The typical waveform of a single pulse received by the receive transducer 21 and imposed on the signal line 57 is indicated by a function "f". The same pulse is repetitively received after the excitation pulse is repetitively launched. The received pulse is sampled at a sequence of time periods labeled $t_0$–$t_{10}$. In other words, rather than trying to do a real-time analog to digital conversion of the signal f, the signal is sampled during individual fixed time periods $t_0$–$t_{10}$ after the transmit pulse is imposed, the analog value during each time period is converted to a digital function, and that data is stored. Thus the total analog waveform response can be recreated from the individual digital values created during each time period t, with the overall fidelity of the recreation of the waveform dependent on the number of time periods t which are sampled. The sampling is not accomplished during a single real time pulse from the receive transducer 21. Instead, a series of pulses are emitted from the transmit transducer 21. The external timer is constructed to provide signals to the sampling A/D converter 42 along signal lines 51 and 52 such that the analog value sampled at time period $t_0$ when the first pulse is applied to a given transducer element, then at time $t_1$ during the second pulse, time $t_2$ during the third pulse, etc. until all the time periods are sampled. Only after the complete waveform has been sampled for each element is the next element, i.e. element b, selected. The output from the A/D converter 42 is provided both to the microprocessor 38 and to the signal processor 41. Thus the digital output values representing the complex waveform f of FIG. 5 can be processed by the signal processor 41 after they are compiled for each transducer element. The waveform can then be analyzed for time delay or attenuation for any given frequency component with respect to the characteristic of the transmitted ultrasonic pulse. The process is then repeated for the other elements until all elements have been utilized to transmit a series of pulses sufficient to create digital data representing the waveform which was received at the receive transducer array 21.

It is this data which may then be utilized in a variety of methods for determining the physical properties of the member. Depending on the manner in which the densitometer is being utilized and the data being sought, the appropriate output can be provided from either the microprocessor 38 or the signal processor 41 through the digital display 18.

Because the ultrasonic pulsing and sampling can be performed so rapidly, at least in human terms, the process of creating a sampled ultrasonic received pulse can optionally be repeated several times to reduce noise by signal averaging. If this option is to be implemented, the process of repetitively launching ultrasonic pulses and sampling the received waveform as illustrated in FIG. 5 is repeated one or more times for each element in the array before proceeding to the next element. Then the sampled waveforms thus produced can be digitally averaged to produce a composite waveform that will have a lesser random noise component than any single sampled waveform. The number of repetitions necessary to sufficiently reduce noise can be determined by testing in a fashion known to one skilled in the art.

Having thus reviewed the internal operation of the densitometer of FIGS. 1–4, it is now possible to understand the methods of use of the densitometer to measure the physical properties of the member. The first method of use involves measuring transit time of an ultrasonic pulse through a subject and comparing that time to the time an ultrasonic pulse requires to travel an equal distance in a substance of known acoustic properties such as water. To use the densitometer in this procedure, the adjustable arm 16 is adjusted until the member of the subject, such as the heel, is clamped between the transducers 21. Then the knob 19 is tightened to fix the adjustable arm in place. The actuator button 12 is then pressed to initiate a pulse and measurement. Next the densitometer is removed from the subject while keeping the knob 19 tight so that the distance between the transducers 21 remains the same. The device 10 is then placed about or immersed in a standard material 32 with known acoustic properties, such as by immersion in a bath of distilled water. The actuator button 12 is pressed again so that acoustic signals are transmitted from the transmit transducer 21 through the material 32 to the receive transducer 21. While it is advantageous to utilize the whole array of elements a through 1 for the measurement of the member, it may only be necessary to use a single pair of elements for the measurement through the standard assuming only that the standard is homogeneous, unlike the member. The signal profiles received by the two measurements are then analyzed by the microprocessor 38 and the signal processor 41. This analysis can be directed both to the comparative time of transit of the pulse through the subject as compared to the standard and to the characteristics of the waveform in frequency response and attenuation through the subject as compared to the standard.

Thus in this method the densitometer may determine the physical properties and integrity of the member 32 by both or either of two forms of analysis. The densitometer may compare the transit time of the acoustic signals through the member with the transmit time of the acoustic signals through the material of known acoustic properties, and/or the device 10 may compare the attenuation as a function of frequency of the broadband acoustic signals through the member 32 with the attenuation of corresponding specific frequency components of the acoustic signals through the material of known acoustic properties. The "attenuation" of an acoustic signal through a substance is the diminution of the ultrasonic waveform from the propagation through either the subject or the standard. The theory and experiments using both of these methods are presented and discussed in Rossman, P.J., Measurements of Ultrasonic Velocity and Attenuation In The Human Os Calcis and Their Relationships to Photon Absorptiometry Bone Mineral Measurements (1987) (a thesis submitted in partial fulfillment of the requirements for the degree of Master of Science at the University of Wisconsin-Madison). Tests have indicated that there exists a linear relationship between ultrasonic attenuation (measured in decibels) (db)) at specific frequencies, and those frequencies. The slope (dB/MHz) of the linear relationship, referred to as the broadband ultrasonic attenuation, is dependent upon the physical properties and integrity of the substance being tested. With a bone, the slope of the linear relationship would be dependent upon the bone mineral density. Thus broadband ultrasonic attenuation through a bone is a parameter directly related to the quality of the cancellous bone matrix.

The microprocessor 38 may therefore be programmed so that the device determines the physical properties and integrity of the member by comparing either relative transit times and/or relative broadband ultrasonic attenuation through the member and a material of known acoustic properties. When comparing the transit times, the microprocessor 38 may be programmed most simply so that the electronics, having received the acoustic signals after they have been transmitted through the member, determines the "member" transit time of those acoustic signals through the member, and after the acoustic signals have been transmitted through the material of known acoustic properties, determines the "material" transit time of the acoustic signals through the material. These time periods may be measured most simply by counting the number of clock pulses of known frequency emitted by the timer 43 between the time of launching the pulse and the sensing of the received pulse at the A/D converter 42. The microprocessor 38 then makes a mathematical "time" comparison of the member transit time to the material transit time and then relates that mathematical time comparison to the physical properties and integrity of the member. The mathematical time comparison may be made by either determining a difference between the member transit time and the material transit time, or by determining a ratio between the member transit time and the material transit time.

As a second method of using the densitometer, it may also determine the physical properties and integrity of the member 32 by determining and comparing the attenuation of the broadband frequency components of the acoustic signals through the member without reference to a material having known acoustic properties. Using this method, the comparison of velocity to a standard is not necessary and absolute transit time of the pulse need not be calculated since it is attenuation that is measured. In such a mode, it is preferable that the transmit transducer 21 transmits an acoustic signal which has a broad range of frequency components, such as a simple ultrasonic pulse. In any case, the acoustic signal should have at least one specific frequency component.

In this attenuation comparison mode, the microprocessor 38 is programmed so that after the receive transducer 21 receives the acoustic signals transmitted through the bone member 32, it determines the absolute attenuation through the member 32 of the frequency component spectrum of the acoustic signals. It is to facilitate the measurement of attenuation that the excitation amplifier circuit 55 and the receiver amplifier 59 have amplification levels which may be digitally controlled. By successively varying the gain of the amplifiers 55 and 59 on successive pulses, the circuit of FIG. 4 can determine what level of gain is necessary to place the peak of the received waveform at a proper voltage level. This gain is, of course, a function of the level of attenuation of the acoustic pulse during transit through the member 32. After the receive transducer 21 receives acoustic signals, microprocessor 38 in conjunction with the signal processor 41 determines the absolute attenuation of individual specific frequency components of the received acoustic signal transmitted through the material. The digital signal processor 41 then makes mathematical "attenuation" comparisons of the corresponding individual specific frequency components through the member. A set of mathematical attenuation comparisons between corresponding frequency components may be thereby obtained, one comparison for each frequency component compared. The manner in which the attenuation functions with respect to frequency can thus be derived. The microprocessor 38 and digital signal processor 41 then relate that function to the physical properties and integrity of the member.

Figure 7:
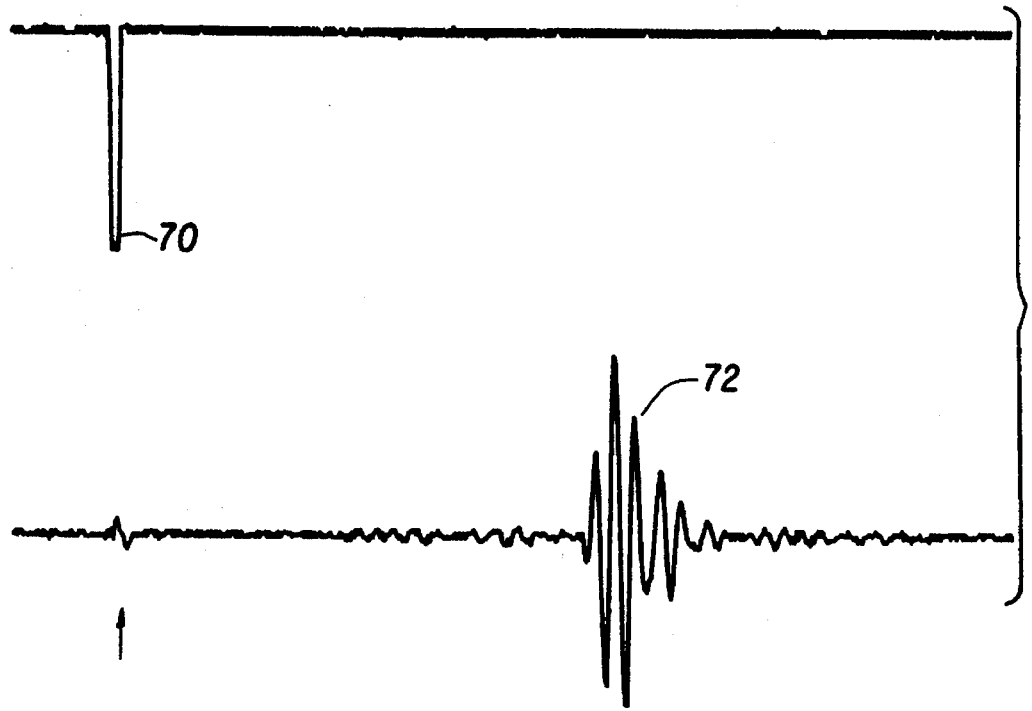
FIG. 7 is a sample of an actual ultrasonic pulse and response from an ultrasonic densitometer according to the present invention.
Figure 8:
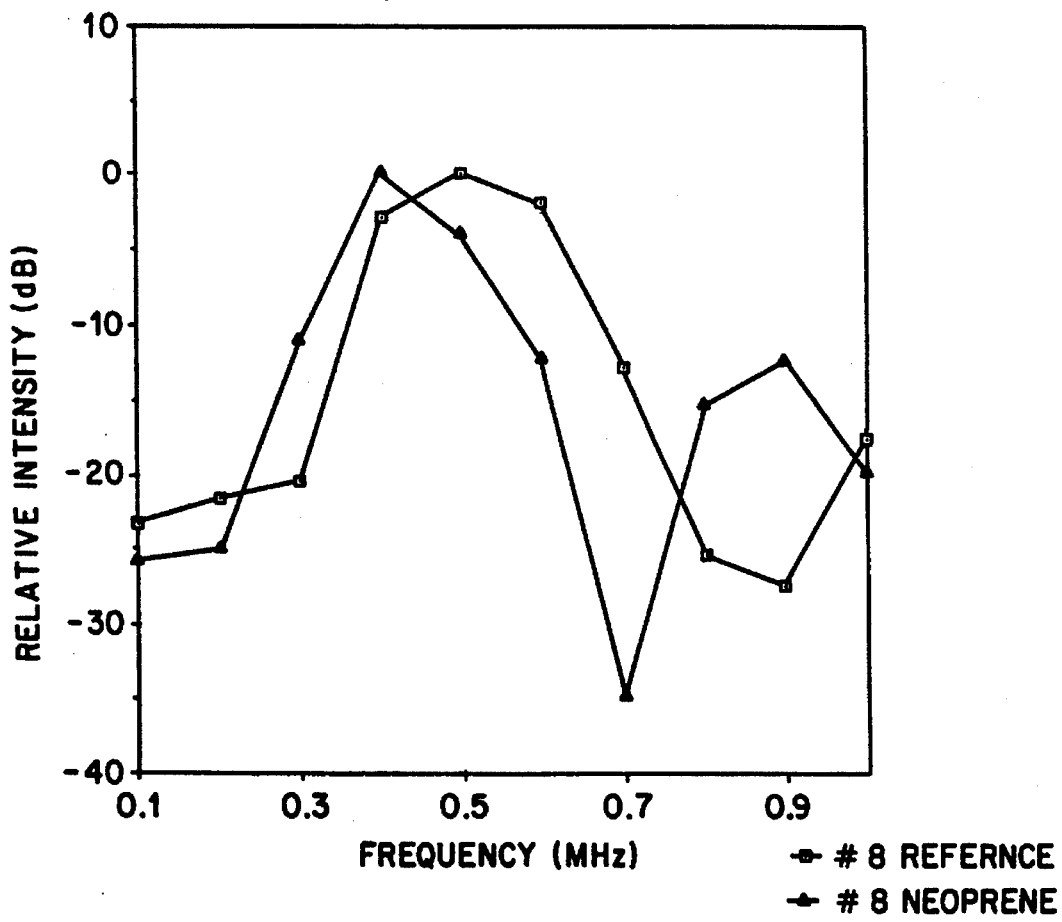
FIG. 8 is a sample plot of relative ultrasound pulse intensity over frequency range.
Figure 9:
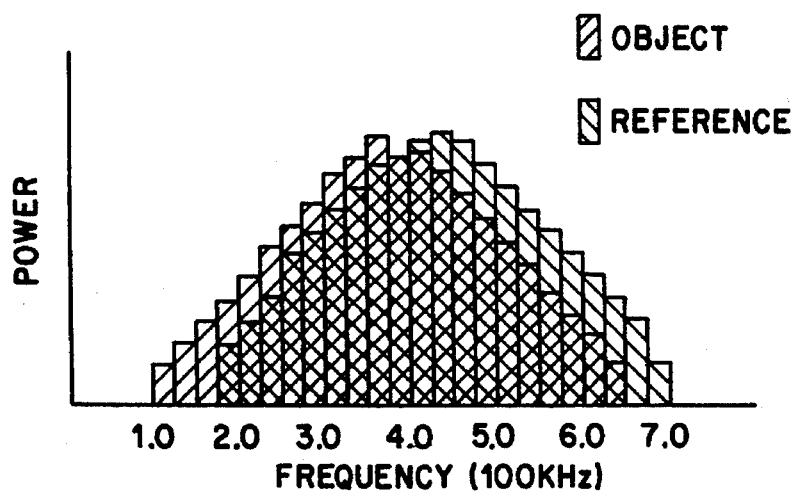
FIG. 9 is a graph in frequency domain illustrating the shift in attenuation versus frequency characteristic of a measured object as compared to a reference.

Shown in FIG. 7 is a sample broadband ultrasonic pulse and a typical received waveform. To achieve an ultrasonic signal that is very broad in the frequency domain, i.e., a broadband transmitted signal, an electronic pulse such as indicated at 70 is applied to the selected ultrasonic transducer in the transmit array 21 which then resonates with a broadband ultrasonic emission. The received signal, such as indicated at 72 in FIG. 7 in a time domain signal plot, is then processed by discrete Fourier transform analysis so that it is converted to the frequency domain. Shown in FIG. 8 is a pair of plots of sample received signals, in frequency domain plots, showing the shift in received signal intensity as a function of frequency between a reference object and a plug of neoprene placed in the instrument. FIG. 9 illustrates a similar comparison, with FIG. 8 using relative attenuation in the vertical dimension and FIG. 9 using power of the received signal using a similar reference material. Both representations illustrate the difference in relative intensities as a function of frequency illustrating how broadband ultrasonic attenuation varies from object to object. The actual value calculated, broadband ultrasonic attenuation, is calculated by first comparing the received signal against the reference signal, then performing the discrete Fourier transform to convert to frequency domain, then performing a linear regression of the difference in attenuation slope to derive broadband ultrasonic attenuation.

The mathematics of the discrete Fourier transform are such that another parameter related to bone member density may be calculated in addition to, or in substitution for, broadband attenuation (sometimes referred to as "attenuation" below). When the discrete Fourier transform is performed on the time-domain signal, the solution for each point includes a real member component and an imaginary member component. The values graphed in FIGS. 8 and 9 are the amplitude of the received pulse as determined from this discrete Fourier transform by taking the square root of the sum of the squares of the real component and the imaginary component. The phase angle of the change in phase of the ultrasonic pulse as it passed through the member can be calculated by taking the arctangent of the ratio of the imaginary to the real components. This phase angle value is also calculated to bone member density.

The microprocessor 38 may also be programmed so that the densitometer simultaneously performs both functions, i.e. determines both transit time and absolute attenuation of the transmitted acoustic signals, first through the member and then through the material with known acoustic properties. The densitometer may then both derive the broadband ultrasonic attenuation function and make a mathematical time comparison of the member transit time to the material transit time. The microprocessor 38 and digital signal processor 41 then relate both the time comparison along with the attenuation function to the physical properties and integrity, or density of the member 32.

In yet another possible mode of operation, the microprocessor 38 may be programmed so that the densitometer 10 operates in a mode whereby the need for calculating either the relative transit time or the attenuation of the acoustic signals through a material of known acoustic properties is eliminated. In order to operate in such a mode, the microprocessor 38 would include a database of normal absolute transit times which are based upon such factors as the age, height, weight, race or the sex of the individual being tested as well as the distance between the transducers or the thickness or size of the member. This database of normal transit times can be stored in the non-volatile memory or could be stored in other media. When testing an individual in this mode, the relevant factors for the individual are placed into the microprocessor 38 to select the pertinent normal transit time based on those factors. The transducers 21 are placed on the bone member being tested as described above. When the actuator button 12 is pressed, the acoustic signals are transmitted through the member 32. The receive transducer 21 receives those signals after they have been transmitted through the member, and the electronics 31 then determine the "member" transit time of the acoustic signals through the member. The microprocessor 38 and digital signal processor 41 then make a mathematical comparison of the measured member transit time to the selected database normal transit time, and relate the mathematical time comparison to the physical properties and integrity, or density of the member, which is displayed.

As an alternative output of the densitometer of the present invention, the digital display 18 could also include a display corresponding to the pattern of the array of elements on the face of the transducer 21 as seen in FIG. 3. This display could then display, for each element a through l, a gray scale image proportional to the parameter, i.e. transit time or attenuation, being measured. This image may provide a visual indication to an experienced clinician as to the physical properties of the member present in the patient.

Figure 6:
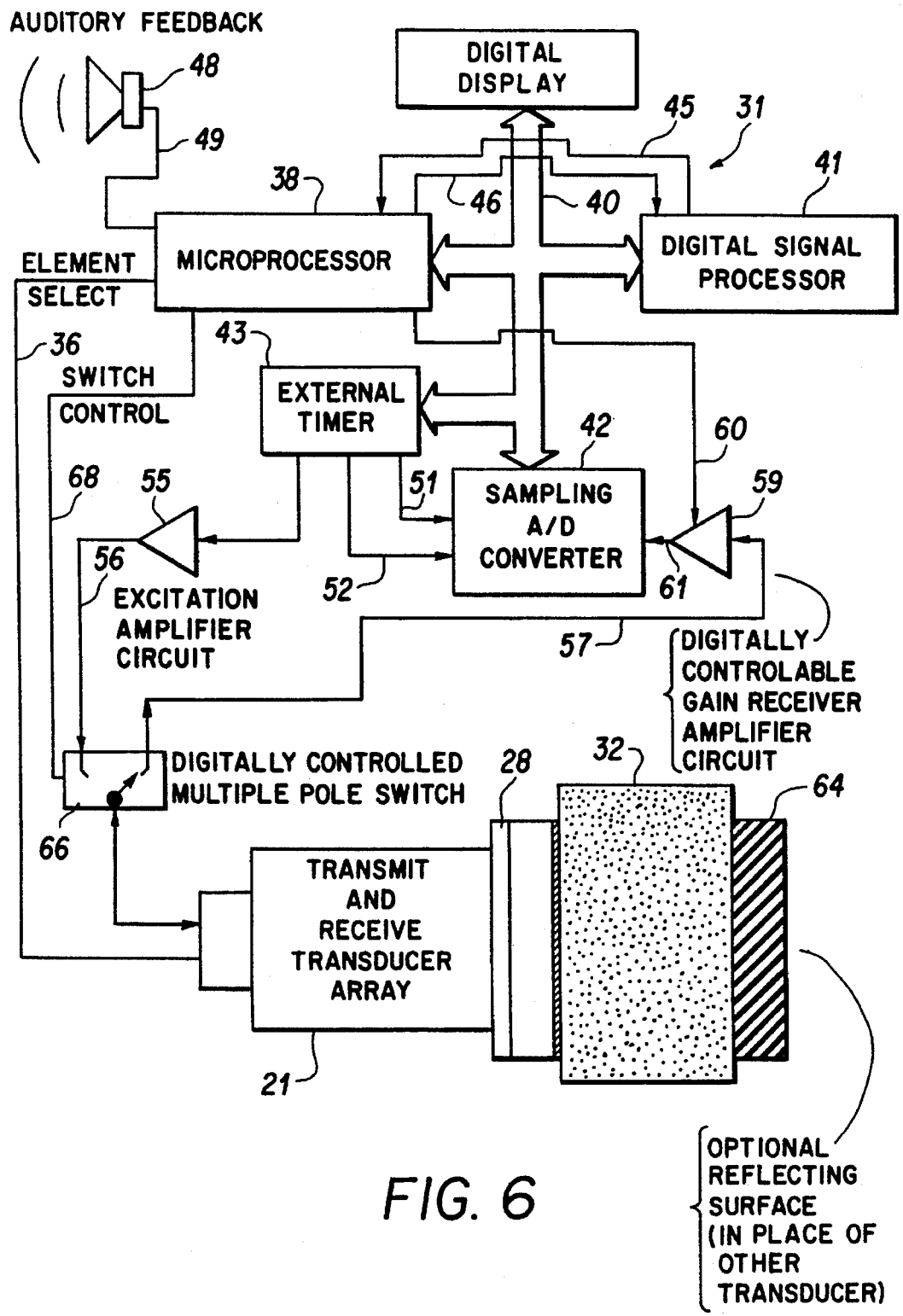
FIG. 6 is a schematic block diagram view of the circuitry of an alternative embodiment of an ultrasound densitometer constructed in accordance with the present invention.

Shown in FIG. 6 is a circuit schematic for an alternative embodiment of an ultrasonic densitometer constructed in accordance with the present invention. In the circuit of FIG. 6, parts having similar structure and function to their corresponding parts in FIG. 4 are indicated with similar reference numerals.

The embodiment of FIG. 6 is intended to function with only a single transducer array 21 which functions both as the transmit and the receive transducer array. An optional reflecting surface 64 may be placed on the opposite side of the member 32 from the transducer array 21. A digitally controlled multiple pole switch 66, preferably an electronic switch rather than a physical one, connects the input to and output from the elements of the transducer array 21 selectively either to the excitation amplifier 55 or to the controllable gain receiver/amplifier circuit 59. The switch 66 is connected by a switch control line 68 to an output of the microprocessor 38.

In the operation of the circuit of FIG. 6, it functions in most respects like the circuit of FIG. 4, so only the differences need be discussed. During the launching of an ultrasonic pulse, the microprocessor 38 causes a signal to appear on the switch control line 68 to cause the switch 66 to connect the output of the excitation amplifier 55 to the selected element in the transducer array 21. Following completion of the launching of the pulse, the microprocessor 38 changes the signal on the switch control line 68 to operate the switch 66 to connect the selected element or elements as an input to the amplifier 59. Meanwhile, the pulse propagates through the member 32. As the pulse transits through the member, reflective pulses will be generated as the pulse crosses interfaces of differing materials in the member and, in particular, as the pulse exits the member into the air at the opposite side of the member. If the transition from the member to air does not produce a sufficient reflective pulse, the reflecting surface 64 can be placed against the opposite side of the member to provide an enhanced reflected pulse.

The embodiment of FIG. 6 can thus be used to analyze the physical properties and integrity of a member using only one transducer 21. All of the methods described above for such measurements may be used equally effectively with this version of the device. The transit time of the pulse through the member can be measured simply by measuring the time period until receipt of the reflected pulse, and then simply dividing by two. This time period can be compared to the transit time, over a similar distance, through a standard medium such as water. The time period for receipt of the reflected pulse could also be simply compared to standard values for age, sex, etc. Attenuation measurements to detect differential frequency measurement can be directly made on the reflected pulse. If no reflecting surface 64 is used, and it is desired to determine absolute transit time, the thickness of the member or sample can be measured.

The use of the multi-element ultrasonic transducer array for the transducers 21, as illustrated in FIG. 3, enables another advantageous feature of the instrument of FIGS. 1–9. Using prior art densitometers, it was often necessary to precisely position the instrument relative to the body member of the patient being measured to have useful results. The difficulty arises because of heterogeneities in the bone mass and structure of actual body members. A measurement taken at one location of density may be significantly different from a measurement taken close by. Therefore prior art instruments fixed the body member precisely so that the measurement could be taken at the precise location each time.

The use of the ultrasonic transducer array obviates the need for this precise positioning. Using the instrument of FIGS. 1–9, the instrument performs a pulse and response, performs the discrete Fourier transform, and generates a value for bone ultrasonic attenuation for each pair of transducer elements a through 1. Then the microprocessor 38 analyzes the resulting array of bone ultrasonic density measurements to reproducibly identify the same region of interest each time. In other words, since the physical array of transducers is large enough to reliably cover at least the one common region of interest each time, the measurement is localized at the same locus each time by electrically selecting the proper location for the measurement from among the locations measured by the array. The instrument of FIGS. 1–9 is conveniently used by measuring the density of the os calcis as measured through the heel of a human patient. When used in this location, it has been found that a region of interest in the os calcis can be located reliably and repeatedly based on the comparisons of bone ultrasonic attenuation at the points in the array. The region of interest in the os calcis is identified as a local or relative minimum in bone ultrasonic attenuation and/or velocity closely adjacent the region of highest attenuation values in the body member. Thus repetitive measurements of the bone ultrasonic attenuation value at this same region of interest can be reproducibly taken even though the densitometer instrument 10 is only generally positioned at the same location for each successive measurement.

This technique of using a multiple element array to avoid position criticality is applicable to other techniques other than the determination of broadband ultrasonic attenuation as described here. The concept of using an array and comparing the array of results to determine measurement locus would be equally applicable to measurements taken of member-density based on speed of sound transit time, other measurements of attenuation or on the calculation of phase angle discussed above. The use of such a multiple-element array, with automated selection of one element in the region of interest, can also be applied to other measurement techniques useful for generating parameters related to bone member density, such as measuring speed changes in the transmitted pulse such as suggested in U.S. Pat. No. 4,361,154 to Pratt, or measuring the frequency of a "sing-around" self-triggering pulse as suggested in U.S. Pat. No. 3,847,141 to Hoop. The concept which permits the position independence feature is that of an array of measurements generating an array of data points from which a region of interest is selected by a reproducible criterion or several criteria. The number of elements in the array also clearly can be varied with a larger number of elements resulting in a greater accuracy in identifying the same region of interest.

In this way, the ultrasound densitometer of the present invention provides a device capable of rapid and efficient determination of the physical properties of a member in vivo without the use Of radiation. Because the densitometer is constructed to operate under the control of the microprocessor 38, it can be programmed to operate in one of several modes, as discussed above. This allows for both flexibility to clinical goals as well as efficient use of the device.

Basin Embodiment

Shown in FIG. 10 is another variation on an ultrasonic densitometer constructed in accordance with the present invention. In the densitometer 100 of FIG. 10, there are two ultrasonic transducer arrays 121, which are generally similar to the ultrasonic transducer arrays 21 of the embodiment of FIG. 1, except that the transducer arrays 21 are fixed in position rather than movable.

The densitometer 100 includes a generally box-shaped mounting case 101 with sloping upper face 102 in which is formed a basin 103. The basin 103 is sized to receive a human foot and is generally trigonous along a vertical plane aligned with the length of the foot so that when the foot is placed within the basin 103, the toes of the foot are slightly elevated with respect to the heel of the foot.

The transducer arrays 121 are positioned in the case 101 so that they extend into the basin 103 to be on opposite sides of the heel of the foot placed in the basin 103. When the foot is in position within the basin 103, the sole of the foot may rest directly on a bottom 104 of the basin 103 with the heel of the foot received within a curved pocket 106 forming a back wall of the basin 103. As so positioned, the transducer arrays 121 are on either side of the os calcis. It has been demonstrated that placing the transducer approximately 4 centimeters up from the sole and 3.5 centimeters forwardly from the rearward edge of the heel places the transducers in the desired region and focused on the os calcis.

The foot may, alternatively, rest on a generally planar foot plate 108 having a contour conforming to the bottom 104 and placed against the bottom 104 between the foot and the bottom 104. The foot plate 108 holds an upwardly extending toe peg 110 for use in reducing motion of the foot during the measurement process. Referring to FIG. 11, the toe peg 110 is sized to fit between the big toe and the next adjacent toe of a typical human foot and is mounted in a slot 112 so as to be adjustable generally along the length of the foot to accommodate the particular length of the foot.

The slot 112 cants inward toward a medial axis 114 of the foot, defined along the foot's length, as one moves along the slot 112 towards the portion of the foot plate 108 near the heel of the foot. This canting reflects the general relation between foot length and width and allows simple adjustment for both dimensions at once.

The toe peg 110 is sized to fit loosely between the toes of the foot without discomfort and does not completely prevent voluntary movement of the foot. Nevertheless, it has been found that the tactile feedback to the patient provided by the toe peg 110 significantly reduces foot movement during operation of the densitometer 100. Two different foot plates 108, being mirror images of each other, are used for the left and right foot.

Referring to FIG. 12, the toe peg 110 is held to the slot 112 by a fastener 111 having a threaded portion which engages corresponding threads in the toe peg 110. The head of the threaded fastener 111 engages the slot 112 so as to resist rotation. Thus, the toe peg 110 may be fixed at any position along the length of the slot 112 by simply turning the toe peg 110 slightly about its axis to tighten the threaded fastener 111 against the foot plate 108.

Referring again to FIG. 10, the basin 103 of the densitometer 110 is flanked, on the upper face 102 of the enclosure 101, by two foot rest areas 116 and 118 on the left and right side respectively. For examination of a patient's right foot, the patient's left foot may rest on foot rest area 118 while the patient's right foot may be placed within basin 103. Conversely, for examination of the patient's left foot, the left foot of the patient is placed within basin 103 and the patient's right foot may rest on foot rest area 116. The foot rest areas have a slope conforming to that of the upper face 102 and approximately that of bottom 104. The flanking foot rest areas 116 and 118 allow the densitometer 100 to be used in comfort by a seated patient.

When the densitometer 100 is not in use, the basin area 103 is covered with a generally planar cover 120 hinged along the lower edge of the basin 103 to move between a closed position substantially within the plane of the upper face 102 and covering the basin 103, and an open position with the plane of the cover 120 forming an angle α with the bottom 104 of the basin 103 as held by hinge stops 122. The angle α is approximately 90° and selected so as to comfortably support the calf of the patient when the patient's foot is in place within basin 103. To that end, the upper surface of the cover 120, when the cover 120 is in the open position, forms a curved trough to receive a typical calf.

The support of the patient's calf provided by the cover 120 has been found to reduce foot motion during operation of the densitometer 100.

Referring now to FIGS. 10 and 12, because the densitometer 100 employs fixed transducers 121, a coupling liquid is provided in the basin 103 to provide a low loss path for acoustic energy between the transducers 121 and the patient's foot regardless of the dimensions of the latter. The coupling liquid is preferably water plus a surfactant, the latter which has been found to improve the signal quality and consistency of the reading of the densitometer. The surfactant may be, for example, a commercially available detergent. It will be recognized, however, that other flowable, acoustically conductive media may be used to provide acoustic coupling, and hence, that the term "coupling liquid" should be considered to embrace materials having a viscosity higher than that of water such as, for example, water based slurries and thixotropic gels.

For reasons of hygiene, the exhaustion of the surfactant, and possible reduction of signal quality with the collection of impurities in the coupling liquid, it has been determined that the liquid in the basin 103 should be changed in between each use of the densitometer 103. Changing this liquid is time consuming and ordinarily would require convenient access to a sink or the like, access which is not always available. Failure to change the liquid may have no immediate visible effect, and hence changing the liquid is easy to forget or delay. For this reason, the present embodiment employs an automated liquid handling system linked to the ultrasonic measurement operation through circuitry controlled by microprocessor 38 to be described.

Figure 13:
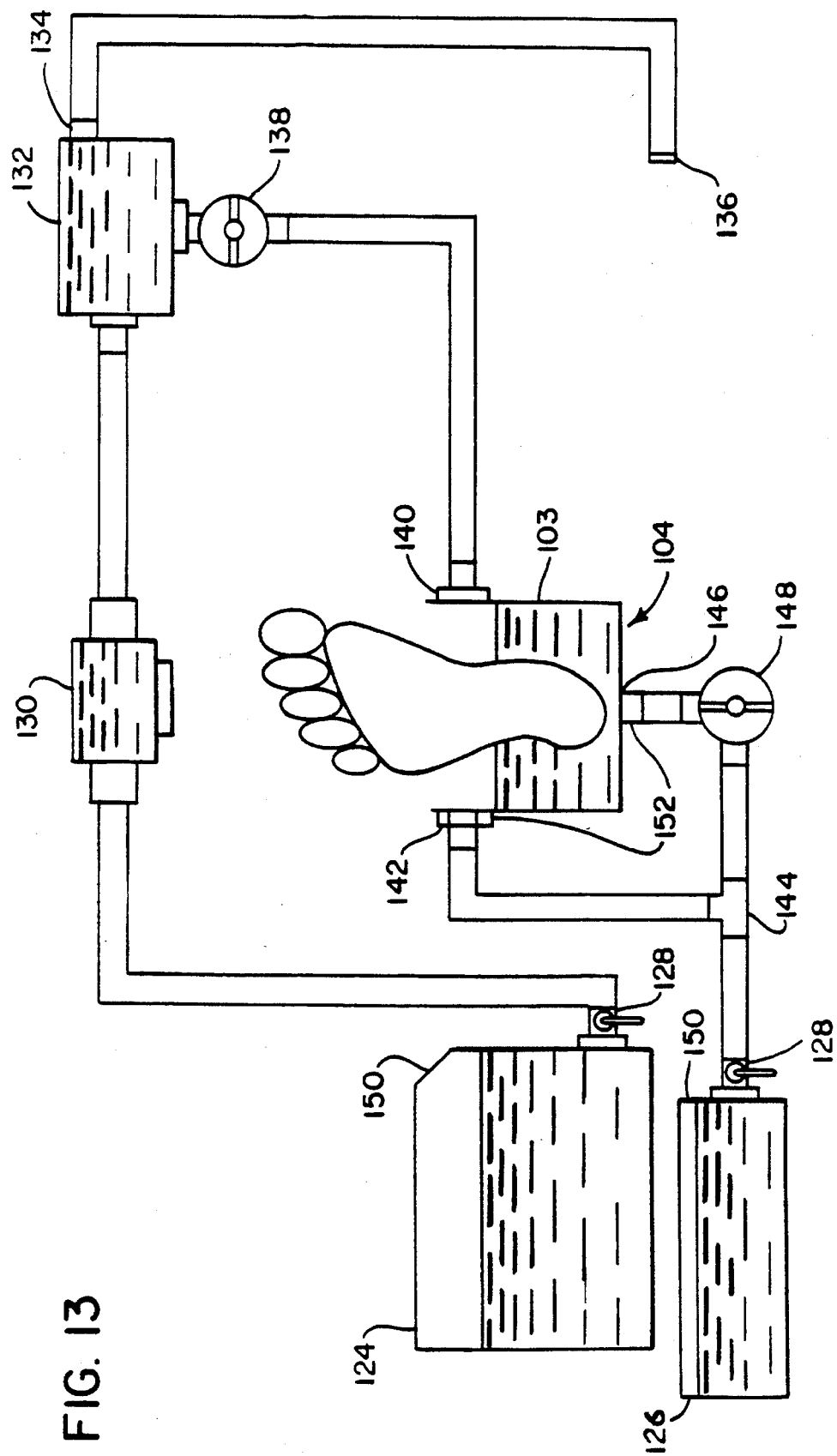
FIG. 13 is a block diagram of a system for transporting the acoustic coupling liquid used in the embodiment of FIG. 10.

Referring to FIG. 13, in the present embodiment, premixed water and surfactant for filling the basin 103 are contained in a removable polypropylene supply tank 124, whereas exhausted water and surfactant from the basin 103 are received by a similar drain tank 126. Each tank 124 and 126 contains a manual valve 128 which is opened when the tanks are installed in the densitometer 100 and closed for transporting the tanks to a remote water supply or drain. The supply tank 124 and the drain tank 126 have vents 150, at their upper edges as they are normally positioned, to allow air to be drawn into or expelled from the interior of the tanks 124 and 126 when they are in their normal position within the densitometer 100 and valves 128 are open. The tanks 124 and 126 hold sufficient water for approximately a day's use of the densitometer 100 and thus eliminate the need for convenient access to plumbing.

The valve 128 of the supply tank 124 connects the tank through flexible tubing to a pump 130 which may pump liquid from the supply tank 124 to a heating chamber 132.

Figure 14:
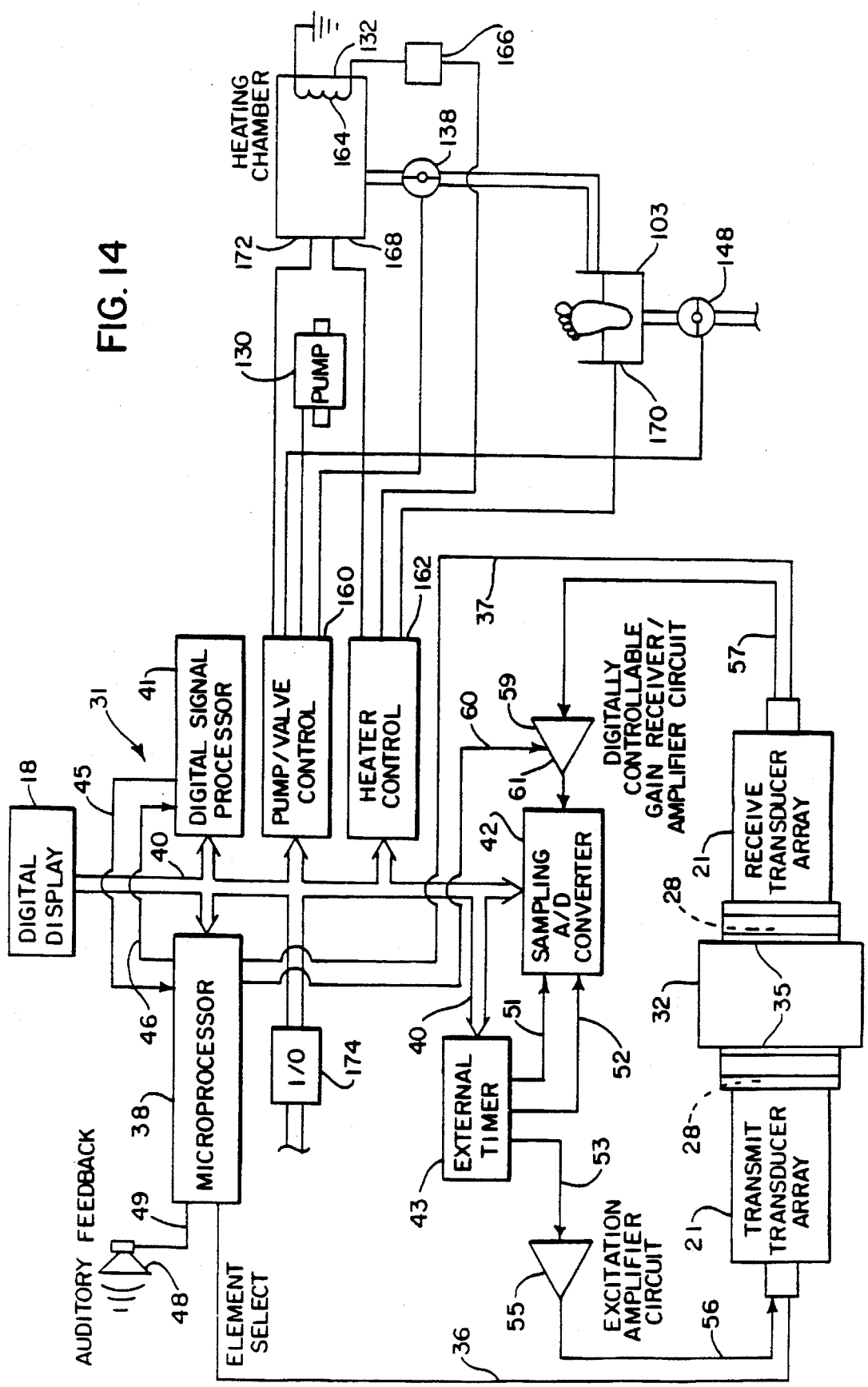
FIG. 14 is a schematic block diagram view of the circuitry of the embodiment of FIG. 10.

Referring to FIG. 14, the heating chamber 132 incorporates a resistive heating element 164 which is supplied with electrical current through a thermal protection module in thermal contact with the coupling liquid in the heating chamber 132. The thermal protection module 166 includes a thermistor and a thermal fuse, as will be described below. A thermistor 168, also in thermal communication with the liquid in the heating chamber, provides a measure of the liquid's temperature during operation of the densitometer 100. The heater chamber 132 additionally incorporates an optical level sensor 172. The level sensor 172 detects the level of liquid in the heating chamber 132 by monitoring changes in the optical properties of a prism system when the prism is immersed in liquid as opposed to being surrounded by air. The operation of the thermistor 168 and the level sensor 172 will be described further below.

Referring again to FIG. 13, the heating chamber 132 communicates through an overflow port 134 and flexible tubing to an overflow drain outlet 136. The overflow outlet 136 is positioned at the bottom of the densitometer 100 removed from its internal electronics. The overflow port 134 is positioned above the normal fill height of the heating chamber 132 as will be described in detail below.

The heating chamber 132 also communicates, through its lowermost point, with an electrically actuated fill valve 138 which provides a path, through flexible tubing, to a fill port 140 positioned in a wall of basin 103.

In the opposite wall of the basin 103 is an overflow port 142 which opens into the basin 103 at a point above the normal fill height of the basin 103 and which further communicates, through a T-connector 144, to the drain tank 126.

A drain 146, in the bottom 104 of the basin 103, provides a path to an electronically actuated drain valve 148. The drain valve 148 operates to allow liquid in the basin 103 to flow through the drain 146 to the T-connector 144 and into the drain tank 126. The overflow port 142 and drain 146 incorporate screens 152 to prevent debris from clogging the tubing or the drain valve 148 communicating with the drain tank 126.

Referring now to FIGS. 10 and 13, the supply tank 124 and the drain tank 126 are positioned within the case 101 Of the densitometer 100 and located at a height with respect to the basin 103 so that liquid will drain from the basin 103 into the drain tank 126 solely under the influence of gravity and so that gravity alone is not sufficient to fill the basin 103 from supply tank 124 when fill valve 138 is open. Further, the heating chamber 132 is positioned above the basin 103 so that once the heating chamber 132 is filled with liquid by pump 130, the filling of the basin 103 from the heating chamber 132 may be done solely by the influence of gravity. Accordingly, the operation of the densitometer in filling and emptying the basin 103 is simple and extremely quiet.

In those situations where plumbing is readily accessible, either or both of the supply and drain tanks 124 and 126 may be bypassed and direct connections made to existing drains or supply lines. Specifically, the pump 130 may be replaced with a valve (not shown) connecting the heating chamber 132 to the water supply line. Conversely, the connection between the T-connector 144 and the drain tank 126 may re-routed to connect the T-conneCtor 144 directly to a drain.

Even with the constant refreshing of the coupling liquid in the basin 103 by the liquid handling system of the present invention, the liquid contacting surfaces of the basin 103, the heating chamber 132, the valves 138 and 148, and the connecting tubing are susceptible to bacterial colonization and to encrustation by minerals. The coatings of colonization or encrustation are potentially unhygienic and unattractive. Sufficient build-up of minerals or bacteria may also adversely affect the operation of the densitometer 100 either by restricting liquid flow through the tubing, by interfering with the operation of the valves 138 or 148, or by adversely affecting the acoustical properties of the transducer array 121.

For this reason, the densitometer 100 is desirably periodically flushed with an antibacterial solution and a weak acid, the latter to remove mineral build-up. These measures are not always effective or may be forgotten, and hence, in the present invention critical water contacting surfaces are treated with a superficial antibacterial material which is also resistant to mineral encrustation. The preferred treatment is the SPI-ARGENT™ surface treatment offered by the Spire Corporation of Bedford, Massachusetts which consists of an ion beam assisted deposition of silver into the treated surfaces. The resulting thin film is bactericidal, fungistatic, biocompatible, and mineral resistant. The properties of being both bactericidal and fungistatic are generally termed infection resistant.

This surface treatment is applied to the water contacting surfaces of the basin 103, the heating chamber 132 and the critical moving components of the valves 138 and 148.

Referring now to FIG. 14, the general arrangement of the electrical components of FIG. 4 is unchanged in the ultrasonic densitometer 100 of FIG. 10 except for the addition of I/O circuitry and circuitry to control the pump 130, valves 138 and 148, and heating chamber 132 of the liquid handling system. In particular, microprocessor 38 now communicates through bus 40 with an I/O module 174, a pump/valve control circuit 160 and a heater control circuit 162.

I/O module 174 provides the ability to connect a standard video display terminal or personal computer to the densitometer 100 for display of information to the user or for subsequent post processing of the data acquired by the densitometer and thus allows an alternative to microprocessor 38 and display 18 for processing and displaying the acquired ultrasound propagation data.

The pump/valve control circuit 160 provides electrical signals to the fill valve 138 and the drain valve 148 for opening or closing each valve under the control of the microprocessor 38. The pump/valve control circuit 160 also provides an electrical signal to the pump 130 to cause the pump to begin pumping water and surfactant from the supply tank 124 under the control of microprocessor 38, and receives the signal from the level sensor 172 in the heating chamber 132 to aid in the control of the pump 130 and valve 138.

The heater control circuit 162 controls the current received by the resistive heating element 164 and also receives the signal from a thermistor 168 in thermal contact with the heating chamber 132. A second thermistor 170, positioned in basin 103 to be in thermal contact with the liquid in that basin 103, is also received by the heater control circuit 162.

Referring now to FIGS. 13 and 14, during operation of the densitometer 100 and prior to the first patient, the basin 103 will be empty, the supply tank 124 will be filled and contain a known volume of water and surfactant, and the drain tanks 126 will be empty. Both manual valves 128 will be open to allow flow into or out of the respective tanks 124 and 126 and the electrically actuated fill valve 138 and drain valve 148 will be closed.

Under control of microprocessor 38, the pump/valve control circuit 160 provides current to the pump 130 which pumps water and surfactant upward into heating chamber 132 until a signal is received from level sensor 172. When the heating chamber 132 is filled to the proper level as indicated by level sensor 172, the signal from level sensor 172 to pump/valve control circuit 160 causes the pump 130 to be turned off. At this time, a predetermined volume of liquid is contained in heating chamber 132 which translates to the proper volume needed to fill basin 103 for measurement.

Under command of microprocessor 38, the heater control circuit 162 provides a current through thermal protection module 166 to resistive heating element 164. The temperature of the liquid in the heating chamber 132 is monitored by thermistor 168 and heating continues until the liquid is brought to a temperature of approximately 39° C. The thermistor and a thermal fuse (not shown) of the thermal protection module 166 provide additional protection against overheating of the liquid. The thermistor opens at 50° C. and resets automatically as it cools and the thermal fuse opens at 66° C. but does not reset and must be replaced. The opening of either the thermistor or the thermal fuse interrupts current to the resistive heating element 164.

When the liquid in the heating chamber 132 is brought to the correct temperature, fill valve 138 is opened by microprocessor 38, through pump/valve control circuit 160, and liquid flows under the influence of gravity into the basin 103 at the proper temperature. The control of the temperature of the liquid serves to insure the comfort of the patient whose foot may be in the basin 103 and to decrease any temperature effects on the sound transmission of the water and surfactant.

Once the heated liquid has been transferred from the heating chamber 132 to the basin 103, the fill valve 138 is closed and the pump 130 is reactivated to refill the heating chamber 132. Thus, fresh liquid for the next measurement may be heated during the present measurement to eliminate any waiting between subsequent measurements.

With liquid in place within the basin 103, the measurement of the os calcis by the densitometer 100 may begin. In this respect, the operation of the ultrasonic densitometer of FIG. 10 is similar to that of the embodiment of FIG. 1 except that the order of pulsing and measurement can be varied. In the apparatus of FIG. 1, the measurement pulse through the member was generally performed before the reference pulse through homogenous standard, i.e. water. In the densitometer 100 of FIG. 10, since the distance between the transducers 121 is fixed, the reference pulse through the homogenous standard material, which is simply the liquid in basin 103, may be conducted before or after a measurement pulse through a live member is performed. In fact, because the temperature of the liquid in the basin 103 is held steady by the temperature control mechanism as described, the standard transmit time measurement can be made once for the instrument and thereafter only measurement pulses need be transmitted.

Preferably, the standard transit time measurement is stored as a number in the memory of microprocessor 38 during the initial calibration of the unit at the place of manufacture or during subsequent recalibrations.

During the calibration of the densitometer 100, the signal from the thermistor 170 is used to produce a transit time corrected for the temperature of the liquid according to well known functional relations linking the speed of sound in water to water temperature. It is this corrected transit time that is stored in the memory associated with microprocessor 38 as a stored standard reference.

The transit time of the measurement pulses is compared to the stored standard reference transit times through the coupling liquid to give an indication of the integrity of the member just measured. Thus, one may dispense with the reference pulse entirely. Empirical tests have determined that by proper selection of a standard reference value stored in the memory of microprocessor 38 and by holding the liquid in the basin within a temperature range as provided by the heating chamber 132, no reference pulse need be launched or measured.

Using this variation, a mathematical comparison of the measured transit time, or transit velocity, must be made to the standard. Since, in the interests of accuracy, it is preferred to use both changes in transit time (velocity) and changes in attenuation to evaluate a member in vivo, the following formula has been developed to provide a numerical value indicative of the integrity and mineral density of a bone:

$$\text{bone integrity value} = (SOS - T)^2 + (BUA/1000) \quad (1)$$

In this formula, "SOS" indicates the speed of sound, or velocity, of the measurement ultrasonic pulse through the member, and is expressed in meters per second. The speed of sound (SOS) value is calculated from the measured transit time by dividing a standard value for the member width by the actual transit time measured. For an adult human heel, it has been found that assuming a standard human heel width of 40 mm at the point of measurement results in such sufficient and reproducible accuracy that actual measurement of the actual individual heel is not needed.

In the above formula, "T" represents a standard minimum value. Two alternative values are possible. One alternative is to set T to the speed of sound value for water, i.e. the reference pulse velocity. This value is about 1500 m/sec for water at 28° C. The principal drawback to this approach is that it has been found, surprisingly, that some people actually have a density value in their heel that is below that of water. For such persons, using the standard water velocity would make the bone integrity value a negative number. Therefore, another alternative is to use the lowest measured human value as T, which in the experience of the investigators here to date is 1475 m/sec.

Lastly in the above formula, BUA is broadband ultrasonic attenuation, as described in greater detail above. The division of 1000 merely scales the influence of the BUA measurement relative to the SOS measurement, which has been determined to be a more effective predictor of bone density.

Measured values of SOS range between 1475 and 1650 m/sec. Measured values of BUA range between 30 and 100 dB/MHz. Using a T=1475, these ranges yield values ranging from very small, i.e. 18, up to relatively large, i.e. around 3000. Thus the bone integrity values obtained exhibit a wide range and are readily comprehensible. It has been determined, again by clinical testing, that persons with a bone integrity value of less than 200 have low spinal bone mineral density, that those in the range of 200–400 have marginal spinal bone mineral density, and that those having bone integrity values of over 400 have acceptable and high levels of spinal bone mineral density.

To verify the accuracy of this approach in predicting spinal bone density, patients were tested using the apparatus of FIG. 10 and also with a dual photon absorptiometry densitometer of accepted standard design. The results of using the ultrasonic densitometer of FIG. 10 have demonstrated that the speed of sound measurement made using this device had a correlation in excess of 0.95 with the measured values of spinal bone density, indicating very good consistency with accepted techniques. However, an occasional patient was tested who exhibited an SOS value in the normal range, but who exhibited a BUA value indicating very poor bone integrity. Accordingly, the bone integrity value was developed to accommodate such deviant results. The value is weighted toward SOS, since that is the principally used reliable predictor value, with a secondary factor including BUA to include such individuals. In fact, the power of the SOS factor may also be increased to the third or fourth power, as opposed to merely the second power, to increase the importance of the SOS term. Since this method utilizing ultrasonic measurement of the heel is quick and free from radiation, it offers a promising alternative for evaluation of bone integrity.

The densitometer 100 may be used with or without an array of ultrasonic transducers in the transducers 121. In its simplest form the mechanical alignment of the heel in the device can be provided by the shape and size of the basin 103. While the use of an array and region-of-interest scanning, as described above, is most helpful in ensuring a reproducible and accurate measurement, mechanical placement may be acceptable for clinical utility in which case only single transducer elements are required.

Upon completion of the measurement, the drain valve 148 is opened by microprocessor 38 through pump/valve control circuitry 160, and the liquid in the basin 103 is drained through "T" 144 to the drain tank 126. At the beginning of the next measurement, the drain valve 148 is closed and liquid is again transferred from the heating chamber 132 as has been described.

With repeated fillings and drainings of the basin 103, the level of liquid in the fill tank 124 decreases with a corresponding increase in the level of the liquid in the drain tank 126. The height of the liquid in each tank 124 and 126 may be tracked by a conventional level sensor such as a mechanical float or a capacitive type level sensor.

Preferably no additional level sensor is employed. The volume of liquid for each use of the densitometer 100 is known and defined by the fill level of the heating chamber 132. The microprocessor 38 may therefore track the level of liquid remaining in the supply tank 124 by counting the number of times the basin 103 is filled to provide a signal to the user, via the display 18 or a remote video display terminal (not shown), indicating that the tanks 124 and 125 need to be refilled and drained respectively. This signal to the user is based on the number of times the basin 103 is filled and a calculation of the relative volumes of the heating chamber 132 and supply tank 124.

After completion of the use of the densitometer 100 for a period of time, the densitometer may be stored. In a storage mode, after both the supply tank 124 and drain tank 126 have been manually emptied, the microprocessor 38 instructs the pump/valve control circuit 160 to open both the fill valve 138 and the drain valve 148 and to run the pump 130. The drain valve 138 is opened slightly before the pump 130 is actuated to prevent the rush of air from causing liquid to flow out of the overflow port 134.

Referring now to FIGS. 10 and 15, the transducers 121 are inserted into the basin 103 through tubular sleeves 180 extending outward from the walls of the basin 103 at the curved pocket along an axis 212 of the opposed transducers 121. The tubular sleeves 180 define a circular bore in which the transducers 121 may be positioned. Each transducers 121 seals the sleeve 180 by compression of o-ring 182 positioned on the inner surface of the sleeve 180.

Although the transducers 121 fit tightly within the sleeves 180, their separation and alignment are determined not by the sleeves 180 but by an independent C-brace 184 comprising a first and second opposed arm 186 separated by a shank 188. A transducers 121 is attached to one end of each of the arms 186, the other ends of the arms 186 fitting against the shank 188.

The arms 186 are generally rectangular blocks transversely bored to receive the cylindrically shaped transducers 121 at one end and to hold them along axis 212. The other ends of the arms 186 provide planar faces for abutting the opposite ends of the block-like shank 188, the abutting serving to hold the arms 186 opposed and parallel to each other.

Although the angles of the arms 186 with respect to the shank 188 are determined by the abutment of the planar faces of the arms 186 and the ends of the shank 188, alignment of the arms 186 with respect to the shank 188 is provided by dowel tubes 190 extending outward from each end of the shank 188 to fit tightly within corresponding bores in the first and second arm 186.

Cap screws 194 received in counterbored holes in the arms 186 pass through the arms 186, the dowel tubes 190 and are received by threaded holes in the shank 188 to hold the arm 186 firmly attached to the shank 188. The dowel tubes 190 and surfaces between the arms 186 and shank 188 serve provide extremely precise alignment and angulation of the transducers 121, and yet a joint that may be separated to permit removal of the transducers 121 from the densitometer 10 for replacement or repair.

Transducers 121 are matched and fitted to the arms 186 in a controlled factory environment to provide the necessary acoustic signal strength and reception. In the field, the shank 188 may be separated from one or both arms 186 by loosening the cap screws 194 so as to allow the transducers 121 extending inward from the arms 186 to be fit within the sleeves 180. Proper alignment and angulation of the transducers is then assured by reattaching the arm or arms 186 removed from the shank 188 to the shank 188 to be tightened thereto by the cap screws 194. Thus, the alignment of the transducers is not dependent on the alignment of the sleeves 180 which may be molded of plastic and thus be of relatively low precision. Nor must alignment be tested while the transducers are in the sleeves 180 attached to the basin 103 but may be checked in a central controlled environment.

Flexible Bladder Embodiment

Referring now to FIGS. 16 and 17, in yet another embodiment of the present invention, the opposed transducers 121 are fitted with annular collars 200 which in turn are attached to flexible bladders 202 extending inward to the basin 103, each bladder 202 containing a liquid or semiliquid coupling "gel" 204.

The bladders 202 serve to contain the gel about the face of the transducers 121 and conform to the left and right sides of a patient's heel 207, respectively, to provide a path between the transducers 121 and the soft tissue and bone of the heel 207 without intervening air. The bladder 202 further prevents the coupling gel 204 from direct contact with the heel and thereby permits the selection of the coupling gel 204 from a broader range of materials.

Compression of the bladders 202 against the heel 207, so as to provide the necessary coupling, is provided by a telescoping shank 181 shown in FIG. 16. In this alternative embodiment of the C-brace 184 of FIG. 15, the shank 188' has been cut into two portions 206 and 208 slidably connected together by dowel pins 210 to provide necessary motion of the transducers 121 inward along their axis to compress the bladders 202 against the heel 207. One end of each dowel pin 210 is press fit within bores in the shank 188' parallel to the axis 212 of the opposed transducers in portion 206. The other ends of the dowel pins 210 slide within larger bores in portion 208 so that portions 208 and 206 may slide toward and away from each other parallel to the axis 212. With such motion, the attached arms 186 move towards and away from each other adjusting the separation of the transducers 121 between an open position for insertion of the heel 207 and a closed position of known separation and orientation where portions 208 and 206 abut.

Control of the separation is provided by means of cam pins 214 protruding from portions 206 and 208 on the side away from the extension of the arms 186 and generally perpendicular to the axis 212. These pins 214 are received by spiral shaped slots in a cam disk 217 fitting over the cam pins 214. The disk includes a radially extending lever 218 whose motion rotates the disk causing the cam pins 214 within the slots 215 to be moved together or apart depending on motion of lever 218.

Thus, the transducers 121 may be moved apart together with the bladders 202 for insertion of the heel 207 into the basin 103. Once the heel is in place, motion of the lever 218 closes the transducers 121 to a predetermined fixed separation compressing the bladders 202 snugly against the sides of the heel 207. The elasticity of the bladder filled with coupling gel 204 provides an expanding force against the heel 207 to closely conform the surface of the bladder 202 to the heel 207.

Cancellation of Heel Width Variations

Figure 18:
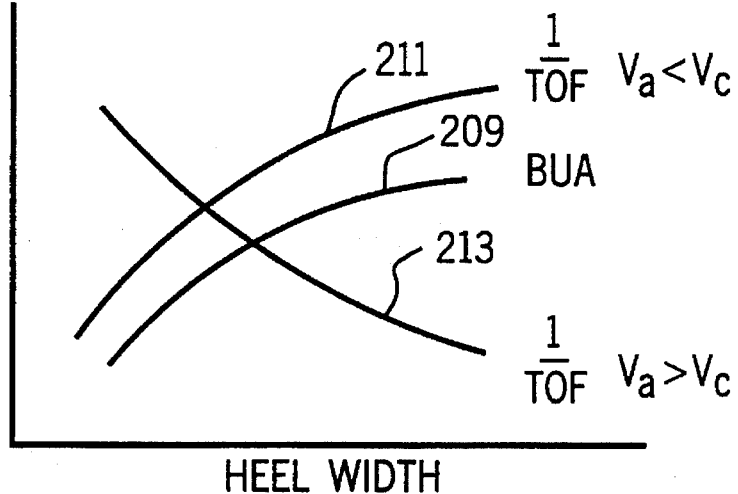
FIG. 18 is a plot of the inverse of time of flight (TOF) for two bone conditions and broadband ultrasonic attenuation (BUA) as a function of heel width showing their opposite functional dependencies.

Referring to FIGS. 17 and 18, generally the thicker the calcaneus 216 of the heel 207, the greater the attenuation of an acoustic signal passing through the heel 207 between transducers 121. Correspondingly, with greater attenuation, the slope of attenuation as a function of frequency, generally termed broadband ultrasonic attenuation (BUA), also increases as shown generally in FIG. 18 by plot 209. This assumes generally that the coupling medium 204 is of low or essentially constant attenuation as a function of frequency. Greater BUA is generally correlated to higher bone quality.

For constant heel thickness, lower TOF (faster sound speed) corresponds generally to higher bone quality. The time of flight (TOF) of an acoustic pulse between the transducers 121 will be proportional to the time of flight of the acoustic pulse through regions A of FIG. 17 comprising the path length through coupling gel 204, regions B comprising the path length through soft tissue of the heel 207 surrounding the calcaneus 216, and region C comprising the path length through the heel bone or calcaneus 216. Thus, $$TOF = \frac{1}{V_A} A + \frac{1}{V_B} B + \frac{1}{V_C} B \quad (2)$$

where $V_A$, $V_B$, and $V_C$ are the average speed of sound through the coupling gel, soft tissue and bone, respectively, and A, B, C are the path lengths through these same materials. Provided that the separation between the transducers 121 is a constant value K, then time of flight will equal:

$$TOF = \frac{1}{V_A} (K - C - B) + \frac{1}{V_B} B + \frac{1}{V_C} B \quad (3)$$

The change in time of flight as a function of thickness of the heel C (the derivative of TOF with respect to C) will thus generally be equal to:

$$\frac{1}{V_C} - \frac{1}{V_A}.$$

Referring now to FIG. 18, if the velocity of sound through the coupling medium 204 is less than that through the bone being measured $$\left( V_A > V_C, \text{ or } \frac{1}{V_C} > \frac{1}{V_A} \right),$$

then the functional relationship of TOF to heel width will be one of increasing as the heel becomes wider (indicated at plot 213 showing values of 1/TOF). On the other hand, if the velocity of sound through the coupling medium 204 is less than that through the bone being measured $$\left( V_C > V_A, \text{ but } \frac{1}{V_A} > \frac{1}{V_C} \right),$$

then the functional relationship of TOF to heel width will be one of decreasing as the heel becomes wider (indicated at plot 211 showing values of 1/TOF).

A combined bone health figure may be obtained by combining BUA and 1/TOF measurements (1/TOF because BUA increases but TOF decreases with healthier bone). Further, if (1) the conditions of ultrasonic propagation are adjusted so that the slope of 1/TOF with heel width is opposite in sign to the slope of BUA with heel width (i.e., $V_A > V_C$) and (2) the BUA and 1/TOF measurements are weighted with respect to each other so that the opposite slopes of the BUA and 1/TOF are equal, then the algebraic combination of the BUA and TOF, through addition for example, will produce a bone quality measurement substantially independent of heel width for a range of bone qualities.

This can be intuitively understood by noting that as the heel gets wider, it displaces some of the coupling gel 204 from between the heel 207 and each transducer 121. By displacing this material (that conducts sound slower than the bone being measured) the total speed with which the sound is conducted is increased.

Note that a similar effect may be obtained by proper scaling and combination of BUA and TOF by multiplication and that other functions of attenuation and TOF could be used taking advantage of their functional independence and their functional dependance in part on heel width.

Figure 19:
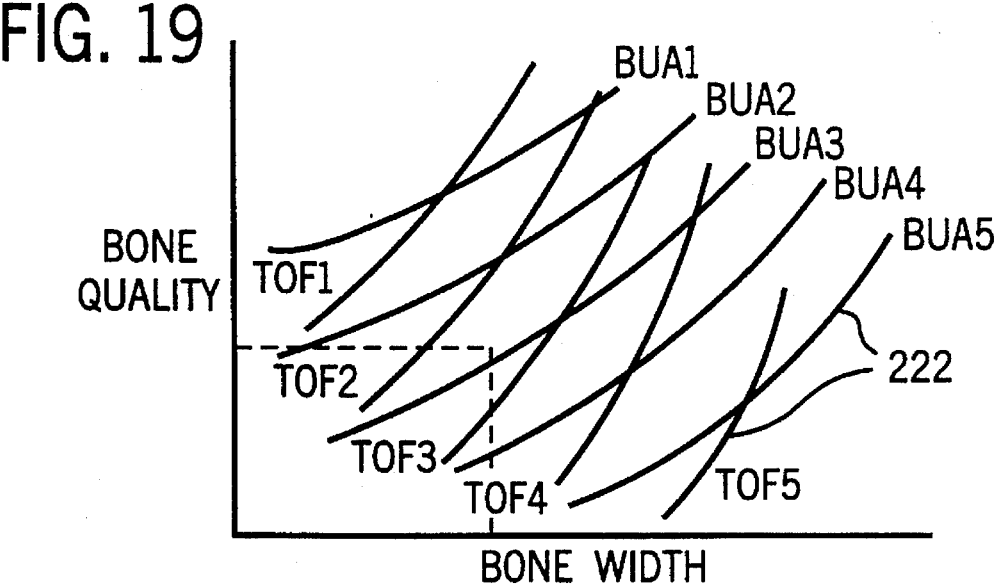
FIG. 19 is a plot of bone quality versus bone width as might be obtained from empirical measurement of multiple bone phantoms and as may be used to eliminate bone width effects in the ultrasonic assessment of bone quality.

Referring now to FIG. 19, more generally BUA and TOF are functionally related to both bone quality and bone width. It should be possible, therefore, to solve the equations governing these relationships for bone quality alone and thus to eliminate the effect of the common variable of heel width. With such an approach, the variable of heel width is eliminated not just for a portion but through the entire range of bone measurement provided that the coupling medium is different from the bone being measured so that there will be a width effect in both BUA and TOF measurements.

Approximations of the algebraic relationships describing the functional dependance of BUA and TOF on bone quality and bone width, can be obtained through the construction of a set of bone phantoms of different widths and bone qualities when using a particular coupling gel. Generally, for each value of BUA or TOF the data will describe a curve 222 linking that value with different combinations of bone quality and bone width. This data may be placed in a look-up table in the memory of the microprocessor of the densitometer as has been previously described.

After BUA and TOF values are determined, the data of the look-up table (for the determined BUA and TOF value) are scanned to find bone quality and width data for the BUA value matching the values of the bone quality and width data for the TOF value. This is equivalent to finding the intersection of the two curves 222 associated with the measured BUA and TOF values. The matching bone quality values of the look-up table will give a bone quality having little or no bone width influence. This value may be displayed to the clinician. It is noted that the previously described technique of summing weighted values of BUA and 1/TOF is but a specialized form of this process of algebraic solution.

Alternatively, a matching bone width value can be identified, being the width of the measured heel, and used to correct either of the BUA or TOF values for display to the clinician in circumstances where BUA or TOF values are preferred for diagnosis.

This ability to cancel out heel width effects will work only for bone qualities where the relationship between the coupling gel 204 and the calcaneus 216 are such as to provide a functional dependance on heel width. Cancellation will not occur, for example, if the density of the calcaneus 216 being measured is substantially equal to the sound speed of the coupling gel 204 and thus where displacement of the coupling gel by similar bone will have no net effect on time of flight. Thus the coupling gel must be properly selected. In this case, materials having higher sound speed may be selected for the coupling material. The difference between the couping gel and the bone being measured will influence the accuracy of the cancellation of heel width effects.

Moderating this desire to improve heel width effects is the importance of keeping the coupling gel 204 close to the acoustic properties of the soft tissue of the heel 207 both to prevent reflection by impedance mismatch and to prevent variations in the thickness of the soft tissue in region B from adding additional uncertainty to the measurement. The coupling medium of water provides good matching to the soft tissue of the heel 207 and has a sound velocity very close to bone and some osteoporotic conditions. Weighting of the attenuation and propagation time may be made for water.

Although the preferred embodiment of the invention contemplates display of a bone quality value or corrected TOF or BUA values, it will be recognized that the same effect might be had by displaying uncorrected BUA or TOF values on a chart and establishing a threshold for healthy or weak bone based on the corrections determined as above.

It is specifically intended that the present invention not be specifically limited to the embodiments and illustrations contained herein, but embrace all such modified forms thereof as come within the scope of the following claims.

We claim:

1. A method of evaluating bone quality of a patient in vivo comprising the steps of:
   (a) positioning the patient's heel along a path of predetermined length greater than the width of the heel;
   (b) determining a measure of transit time of an ultrasonic pulse for the predetermined path length through a standard coupling medium and the heel, the coupling medium conducting sound at a predetermined first sound speed;
   (c) determining a measure of attenuation of the ultrasonic pulse for the predetermined path length through the coupling medium and the heel, the coupling medium attenuating sound at a predetermined first attenuation rate; and
   (d) evaluating the functional relationship between the measure of attenuation and bone quality and heel width for the predetermined length and the coupling medium, and the functional relationship between the measure of transit time and bone quality and bone heel, for the predetermined length and the coupling medium, to identify a single pair of common bone quality and heel width values related to both of the measures of attenuation and transit time, the common bone quality value being substantially independent of the width of the heel.

2. The method of claim 1 wherein the measure of attenuation is the slope of attenuation of the ultrasonic pulse as a function of frequency (BUA) as it crosses the heel and wherein the measure of transit time is the time taken for the ultrasonic pulse to cross the heel.

3. The method of claim 1 including the additional step of:
   (e) displaying the common bone quality value.

4. The method of claim 1 including the additional step of:
   (e) displaying the measure of attenuation and the measure of transit time together with a threshold indicating bone quality wherein the threshold is based on the common bone quality value.

5. The method of claim 1 wherein the step of evaluation is provided by a predetermined algebraic combination of the measure of attenuation and the measure of transit time.

6. The method of claim 1 wherein the step of evaluation reviews a data base of bone quality values and heel width values linked to ones of the measures of attenuation and transit time to find a common pair of bone quality value and heel width values related to both the measures of attenuation and transit time.

7. The method of claim 1 including the additional step of:
   (e) correcting the attenuation value for the effects of heel width using the common heel width value.

8. The method of claim 7 including the additional step of:
   (e) displaying the corrected attenuation value.

9. The method of claim 7 including the additional step of:
   (e) displaying the measure of attenuation together with a threshold indicating bone quality wherein the threshold is based on the corrected attenuation value.

10. The method of claim 1 including the additional step of:
    (e) correcting the transit time value for the effects of heel width using the common heel width value.

11. The method of claim 10 including the additional step of:
    (e) displaying the corrected transit time value.

12. The method of claim 10 including the additional step of:
    (f) displaying the measure of attenuation together with a threshold indicating bone quality wherein the threshold is based on the corrected attenuation value.

13. The method of claim 1 including the additional step of:
    (e) displaying the common heel width value.

14. An ultrasonic densitometer for measuring bone integrity comprising:
    a water basin sized to receive the heel of a patient, the basin having opposed first and second openings along an axis intersecting the patient's heel when the patient's heel is in place within the basin;
    a first and second ultrasonic transducer sized to be slidably received in the first and second opening respectively;
    a C-brace removable from the water basin and having a first and second arm attachable to the first and second transducer and having at least one separable joint so that the first and second arm may be moved apart for insertion of the first and second transducers into the first and second openings, the separable joint further having alignment surfaces causing the first and second ultrasonic transducer to be returned to a predetermined alignment and separation when the alignment surfaces abut.

* * * * *